United States Patent
Jouhikainen et al.

(10) Patent No.: US 10,405,813 B2
(45) Date of Patent: Sep. 10, 2019

(54) PANORAMIC IMAGING USING MULTI-SPECTRAL X-RAY SOURCE

(71) Applicants: Dental Imaging Technologies Corporation, Hatfield, PA (US); PaloDEx Group OY, Tuusula (FI)

(72) Inventors: Petri Jouhikainen, Jarvenpaa (FI); David Albert Sebok, Eagleville, PA (US); Bradley S. Carlson, Doylestown, PA (US); Hongjian Shi, Souderton, PA (US); Mike Parma, Chalfont, PA (US); Edward Marandola, Gwynedd, PA (US); Robert Keating, Chalfont, PA (US); Esa Suuronen, Kerava (FI); Scott Kravis, West Caldwell, NJ (US)

(73) Assignees: Dental Imaging Technologies Corporation, Hatfield, PA (US); PaloDEx Group OY, Tuusula (FI)

( * ) Notice: Subject to any disclaimer, the term of this patent is extended or adjusted under 35 U.S.C. 154(b) by 651 days.

(21) Appl. No.: 14/614,250

(22) Filed: Feb. 4, 2015

(65) Prior Publication Data

US 2016/0220207 A1    Aug. 4, 2016

(51) Int. Cl.
   *A61B 6/14*    (2006.01)
   *A61B 6/00*    (2006.01)
   (Continued)

(52) U.S. Cl.
   CPC ............... *A61B 6/14* (2013.01); *A61B 6/405* (2013.01); *A61B 6/4007* (2013.01);
   (Continued)

(58) Field of Classification Search
   CPC ........... A61B 6/14; A61B 6/40; A61B 6/4007; A61B 6/4021; A61B 6/4028;
   (Continued)

(56) References Cited

U.S. PATENT DOCUMENTS

| 4,606,061 A | 8/1986 | Ramamurti |
| 4,731,807 A | 3/1988 | Plessis et al. |

(Continued)

FOREIGN PATENT DOCUMENTS

| EP | 1961383 A1 | 8/2008 |
| EP | 2192422 A1 | 6/2010 |

(Continued)

OTHER PUBLICATIONS

Partial European Search Report from the European Patent Office for Application No. 16154275.8 dated Jun. 8, 2016 (6 pages).

(Continued)

*Primary Examiner* — Anastasia Midkiff
(74) *Attorney, Agent, or Firm* — Michael Best & Friedrich LLP

(57) ABSTRACT

Systems and methods for obtaining a panoramic image are provided. One system includes a gantry, an x-ray source, a receptor, and at least one controller. The x-ray source is mounted on the gantry and is configured to alternatively output x-ray radiation at a first energy level and x-ray radiation at a second energy level. The receptor is mounted on the gantry so that x-ray radiation from the x-ray source impinges on the receptor. The receptor is configured to output a plurality of frames of data including a first frame and a second frame sequential to the first frame. The controller is configured to control the x-ray source so that data in the first frame is generated based on x-ray radiation of the first energy level and data in the second frame is based on x-ray radiation of the second energy level.

42 Claims, 21 Drawing Sheets

(51) Int. Cl.
*A61C 19/04* (2006.01)
*A61B 5/00* (2006.01)

(52) U.S. Cl.
CPC .......... *A61B 6/4021* (2013.01); *A61B 6/4035* (2013.01); *A61B 6/4241* (2013.01); *A61B 6/482* (2013.01); *A61C 19/04* (2013.01); *A61B 5/4547* (2013.01); *A61B 6/5235* (2013.01); *A61B 6/542* (2013.01); *G01N 2223/423* (2013.01)

(58) Field of Classification Search
CPC ..... A61B 6/4035; A61B 6/405; A61B 6/4241; A61B 6/44; A61B 6/48; A61B 6/482; A61B 6/52; A61B 6/5211; A61B 6/5241; A61B 2560/00; A61B 2560/02; A61B 2560/0204; A61B 2560/0214; A61B 5/45; A61B 5/4538; A61B 5/4542; A61B 5/4547; A61C 1/088; A61C 19/04; A61N 2005/0626; A61N 2005/0629; A61N 2005/0632; A61N 2005/0635; A61N 2005/0664; A61N 2005/0667; H01J 1/32; H01J 1/34; H01J 1/35; H01J 1/46; H01J 1/50; H01J 3/00; H01J 3/02; H01J 3/021; H01J 3/027; H01J 3/06; H01J 3/26; H01J 3/30; H01J 3/32; H01J 19/00; H01J 19/02; H01J 19/04; H01J 19/08; H01J 19/14; H01J 19/28; H01J 19/32; H01J 19/38; H01J 19/66; H01J 19/78; H01J 19/82; H01J 21/02; H01J 21/22; H01J 35/00; H01J 35/02; H01J 35/025; H01J 35/04; H01J 35/045; H01J 35/06; H01J 35/065; H01J 35/08; H01J 35/14; H01J 35/24; H01J 35/28; H01J 35/30; H01J 37/00; H01J 37/02; H01J 37/04; H01J 37/06; H01J 37/063; H01J 37/073; H01J 37/075; H01J 37/10; H01J 37/12; H01J 37/14; H01J 37/141; H01J 37/143; H01J 37/145; H01J 37/24; H01J 37/241; H01J 37/248; H01J 2203/02; H01J 2203/0208; H01J 2235/00; H01J 2235/02; H01J 2235/06; H01J 2235/064; H01J 2235/066; H01J 2235/08; H01J 2235/081; H01J 2235/086; H01J 2235/088; H01J 2893/0064; H01J 2893/0065; H01J 2893/0068; H01J 2893/0048; H01J 2893/005; H01J 2893/0051; H01J 2893/0053; H01J 2893/0058; H01J 2237/2445; H01J 2237/245; H01J 2237/24507; H01J 2237/248; H01J 2237/2485; H01J 3/19; H01J 3/04; H01J 3/08; H01J 3/14; H01J 3/28; H01J 3/38; H01J 3/66; H01J 3/78; H01J 3/82; H01J 2237/04; H01J 2237/06; H01J 2237/063; H01J 2237/06308; H01J 2237/06325; H01J 2237/06333; H01J 2237/06358; H01J 2237/15; H01J 2237/1501; H01J 2237/1504; H01J 2237/1508; H01J 2237/151; H01J 2237/152; H01J 2237/244; H01J 2237/241; H01J 2237/24415; H01J 2237/2442; G01N 23/087; G01N 2223/20; G01N 2223/30; G01N 2223/304; G01N 2223/423–425; G01N 2223/427; G01N 2223/612; G01N 2223/6123; G05F 3/222; G05F 3/227; G05F 1/00; G05F 1/10; G05F 1/40; G05F 1/462; G05F 1/468; G05F 1/565; G05F 1/613; G05F 1/625; H02J 1/00; H02J 3/38; H02J 3/381; H02J 7/007; H02J 2001/008; H02M 1/088; H02M 3/156; H02M 2001/0003; H02M 2001/0006; H02M 2001/096; H05G 1/00; H05G 1/02; H05G 1/08; H05G 1/085; H05G 1/10; H05G 1/26; H05G 1/28; H05G 1/30; H05G 1/32; H05G 1/52; H05G 1/56; H05G 1/60

See application file for complete search history.

(56) References Cited

U.S. PATENT DOCUMENTS

| | | | |
|---|---|---|---|
| 5,305,363 A * | 4/1994 | Burke | A61B 6/032 378/10 |
| 5,864,146 A | 1/1999 | Karellas | |
| 7,203,273 B2 | 4/2007 | Linnosaari | |
| 7,783,002 B2 * | 8/2010 | Savinen | A61B 6/14 378/19 |
| 8,325,874 B2 * | 12/2012 | Shi | A61B 6/14 378/38 |
| 8,548,120 B2 * | 10/2013 | Shi | A61B 6/14 378/38 |
| 8,693,748 B2 * | 4/2014 | Jouhikainen | A61B 1/00 382/128 |
| 2004/0247082 A1 | 12/2004 | Hoffman | |
| 2006/0115049 A1 | 6/2006 | Linnosaari | |
| 2006/0134000 A1 | 6/2006 | Heismann | |
| 2010/0191107 A1 * | 7/2010 | Bowers | A61B 5/0091 600/436 |
| 2011/0007874 A1 * | 1/2011 | Vogtmeier | H01J 1/3048 378/119 |
| 2011/0176717 A1 * | 7/2011 | Siren | A61B 6/032 382/131 |
| 2011/0305320 A1 * | 12/2011 | Suuronen | A61B 6/00 378/98.5 |
| 2013/0039474 A1 * | 2/2013 | Turqueti | H01J 35/065 378/124 |
| 2013/0051532 A1 * | 2/2013 | Caiafa | H01J 35/18 378/110 |
| 2014/0105370 A1 | 4/2014 | Yamakawa et al. | |
| 2014/0225892 A1 * | 8/2014 | Parma | G06T 7/0012 345/426 |

FOREIGN PATENT DOCUMENTS

| | | |
|---|---|---|
| JP | 2007319575 A | 12/2007 |
| JP | 2008-016339 A | 1/2008 |
| JP | 2010-158392 A | 7/2010 |
| JP | 2014161590 A | 9/2014 |
| WO | 02/006767 A1 | 1/2002 |
| WO | 2012/088243 A2 | 6/2012 |
| WO | 2013095706 A1 | 6/2013 |
| WO | 2014181889 A1 | 11/2014 |

OTHER PUBLICATIONS

Extended European Search Report from the European Patent Office for Application No. 16154275.8 dated Aug. 22, 2016 (13 pages).
Japanese Patent Office Action for Application No. 2016-014157 dated Dec. 25, 2018 (8 pages, English translation included).

* cited by examiner

PANORAMIC IMAGING USING MULTI-SPECTRAL X-RAY SOURCE

BACKGROUND

The present invention relates to x-ray imaging. More particularly, embodiments of the present invention related to panoramic x-ray imaging, including but not limited to frame-based, panoramic imaging.

In many x-ray imaging systems, an x-ray source is operated to generate x-ray energy within a single spectral band (or spectrum). However, x-ray sources can also be operated to generate x-ray output within two (and possibly more) spectral bands (or spectra). Typically, each spectral band is centered about a different energy level.

SUMMARY

Multi-spectral imaging has been used in certain 2D radiography and 3D computer tomography ("CT") imaging systems, in some cases utilizing two bands and referred to as dual energy imaging. However, multi-spectral imaging techniques have not, in general, been applied to panoramic imaging. One reason for not implementing multi-spectral techniques is that traditional time-delay integration ("TDI") techniques have not been readily compatible with the use of a multi-spectral source. Another reason relates to the frame-rate requirements for panoramic imaging. Generally, the high frame rates used in panoramic imaging have been achievable only with continuously operating or "on" x-ray sources with a single spectral output, rather than pulsed x-rays. A reason for this is that the time required to turn the x-ray source on and off is unacceptably long with conventional x-ray tube technology. Alternatively, or in addition, it is possible to use two separates scans (each at a different spectral energy). However, this approach has undesirable effects associated with patient movement between the scans.

Accordingly, the present invention provides methods for multi-spectral panoramic imaging that allow frame rates fast enough to image without patient motion effects. In one embodiment, the invention provides a panoramic x-ray system. The system includes a gantry, an x-ray source, a receptor, and a controller. The x-ray source is mounted on the gantry and is configured to alternatively output at least x-ray radiation at a first energy level and x-ray radiation at a second energy level. The receptor is mounted on the gantry so that x-ray radiation from the x-ray source impinges the receptor. The receptor is configured to output a plurality of frames of data including a first frame and a second frame sequential to the first frame. The controller is configured to control the x-ray source so that data in the first frame is generated based on x-ray radiation of the first energy level and data in the second frame is based on x-ray radiation of the second energy level. New technology is implemented that allows acceptably rapid switching of the x-ray radiation.

Another embodiment of the invention provides a panoramic x-ray system that includes a gantry, a multi-spectral x-ray source, a detector panel, and a controller. The multi-spectral x-ray source is mounted on the gantry and is configured to output x-ray radiation that includes radiation at first and second energy levels. The radiation produced by the source need not be limited to the first and second energy levels, but can also include radiation at other energy levels. The controller is configured to control the x-ray source to generate the x-ray radiation. The detector panel is mounted on the gantry so that x-ray radiation from the x-ray source impinges the receptor. The detector panel is configured to distinguish between radiation at the first energy level and the second energy level and output a plurality of frames of data including a first frame and a second frame sequential to the first frame.

In another embodiment, the invention provides a method of obtaining a panoramic image from a plurality of projection frames. The method includes generating x-ray radiation at a first energy level, detecting a first frame of data based on the x-ray radiation at the first energy level impinging a receptor, generating x-ray radiation at a second energy level, detecting a second frame of data, sequential to the first frame of data, based on the x-ray radiation at the second energy level impinging the receptor, and, after acquiring a plurality of such frames at each energy level), generating a panoramic image based on the plurality of frames.

Optionally, the energy or spectrum of the radiation emitted by the x-ray source can be varied from frame to frame by changing the cathode-anode voltage of the source between frames.

Other aspects of the invention will become apparent by consideration of the detailed description and accompanying drawings.

DETAILED DESCRIPTION

Figure 1A:
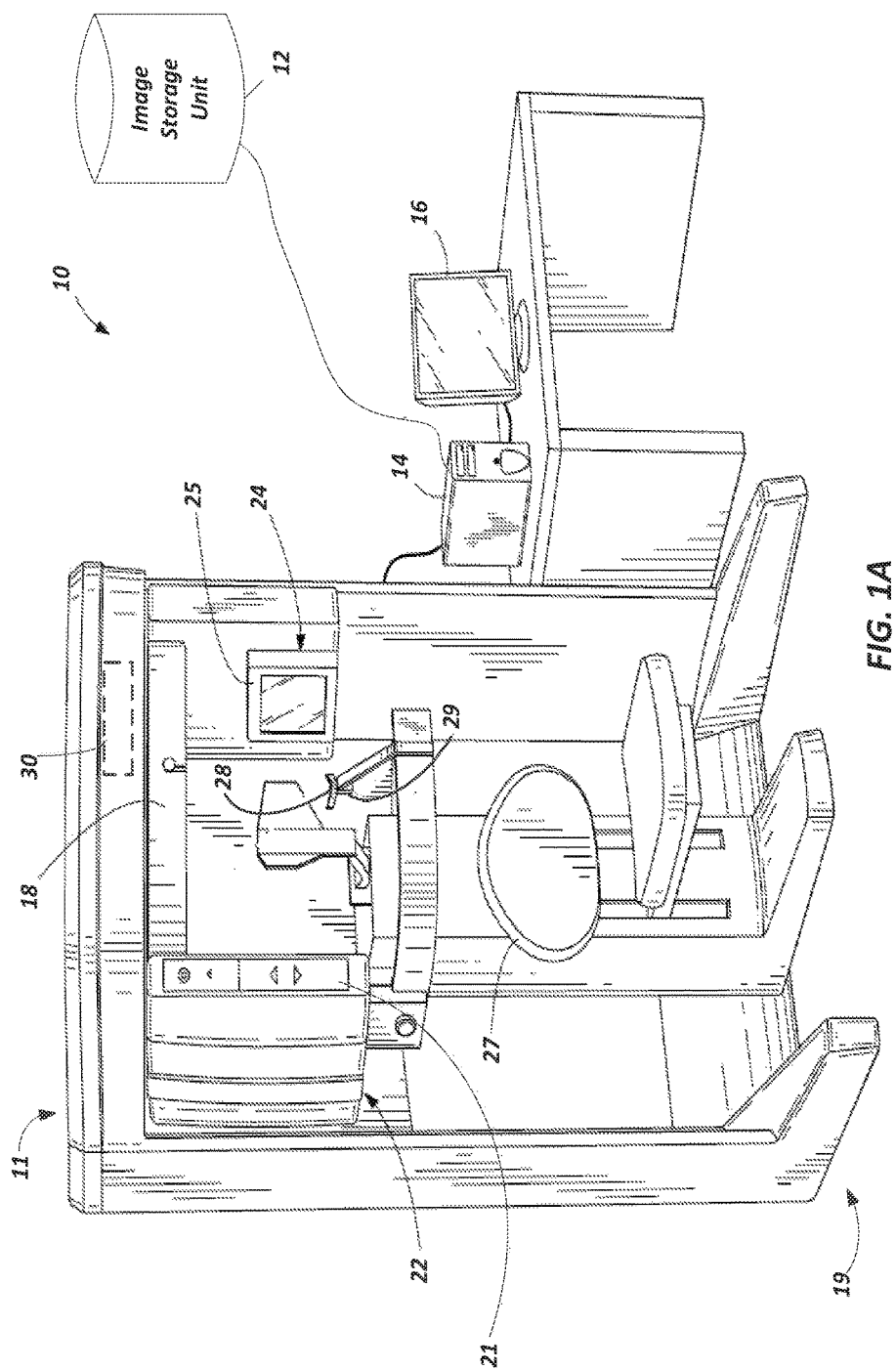
FIG. 1A schematically illustrates a multi-spectral panoramic imaging system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. The terms "mounted," "connected," and "coupled" are used broadly and encompass both direct and indirect mounting, connecting, and coupling. Further, "connected" and "coupled" are not restricted to physical or mechanical connections or couplings, and can include electrical connections or couplings, whether direct or indirect. Also, electronic communications and notifications may be performed using known means including wired connections, wireless connections, etc.

It should be noted that a plurality of hardware- and software-based devices, as well as a plurality of different structural components may be utilized to implement the invention. Furthermore, and as described in subsequent paragraphs, the specific configurations illustrated in the drawings are intended to exemplify embodiments of the invention and that other alternative configurations are possible.

FIG. 1A illustrates an imaging system 10. The system 10 includes an imaging apparatus 11, an image storage unit 12, and a host computer 14. As illustrated in FIG. 1A, the image storage unit 12 can be located remote from the imaging apparatus 11, and can be connected to the host computer 14 via a wired connection, a wireless connection, or a combination thereof. In other embodiments, the image storage unit 12 is included in the host computer 14. At least one peripheral device can be coupled to the host computer 14. For example, as illustrated in FIG. 1A, a display device 16 that allows a user to view the images is coupled to the host computer 14. In some embodiments, additional peripheral devices are coupled to the host computer 14, e.g., a keyboard, a mouse, a printer, etc. Also, in some embodiments, the display 16 includes a touch-sensitive screen.

The imaging apparatus 11 includes a gantry 18, a supporting base 19, an operator panel 21, and a controller 30. Optionally, the controller 30 can be inside the housing of the imaging apparatus, as illustrated in FIG. 1A. The gantry 18 supports an x-ray source or sources 22 and an x-ray receptor 24. The x-ray receptor 24 is positioned opposite to and facing the x-ray source 22 and includes a receptor array 25 having a plurality of detection elements. During a scan, a patient either sits on a chair or other support 27 (which is optional) or stands up. Optionally, the patient places his or teeth around a bite stick 28 and/or places his or her chin in a chin support 29. The gantry 18 is rotated around the patient's head. As the gantry 18 rotates, the x-ray source 22 moves and directs radiation at the patient's head at various angles. Optionally, the center of rotation of the gantry can be translated to optimize the respective positions of the source 22 and receptor array 25. The x-ray receptor array 25 detects the radiation passing through the patient and generates a panoramic data set comprising a plurality of projection frames.

Figure 1B:
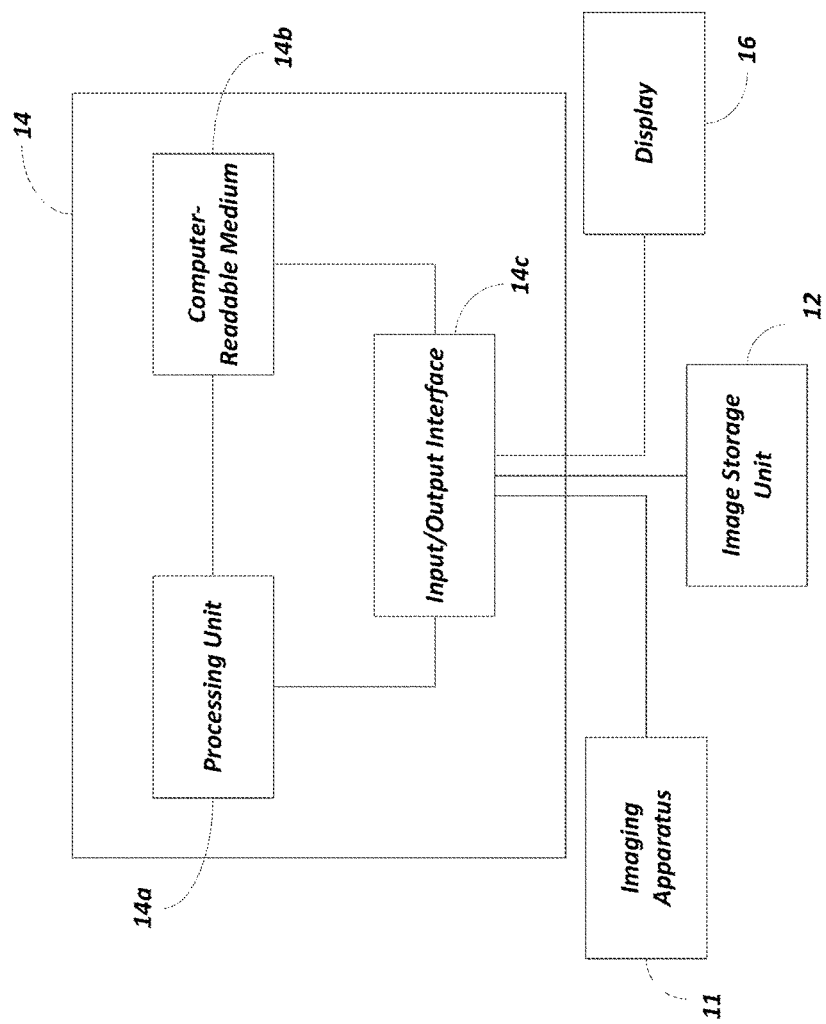
FIG. 1B schematically illustrates a host computer included in the system of FIG. 1A.

Information gathered by the x-ray receptor array 25 is sent to the host computer 14. The host computer 14 may also store information regarding operation of the imaging apparatus 11,—e.g., the position of the gantry 18 and/or the energy of the x-ray radiation emitted by the x-ray source 22. As illustrated in FIG. 1B, the host computer 14 includes a processor 14a, non-transitory computer-readable medium 14b, and an input/output interface 14c. It should be understood, however, that in other constructions, the imaging processing unit 14 includes additional, fewer, or different components.

The processor 14a is configured to retrieve instructions and data from the medium 14b and execute, among other things, instructions to receive a data set from the imaging apparatus 11, process the data set to generate images, output the images to the display 16 (i.e., generate a signal for displaying data on the display 16), and output data to the image storage unit 12. The input/output interface 14c transmits data from the processor 14a to external systems, networks, and/or devices and receives data from external systems, networks, and/or devices. In particular, the input/output interface 14c communicates with the imaging apparatus 11, the display 16, and image storage unit 12 over one or more wired or wireless connections and/or networks. The input/output interface 14c can also store data received from external sources to the medium 14b and/or provide the data to the processor 14a.

The x-ray source 22 generates x-rays or x-ray radiation. X-rays are a form of electromagnetic energy (photons of a certain energy) used in medical applications involving the visualization of structures within a patient's body. As is known, when a patient's body or part thereof is exposed to x-ray radiation (photons of a certain energy), a certain portion of the radiation passes through the body and is detected by the x-ray receptor 24. Another portion of the radiation is absorbed. The actual amount of radiation that makes it through the body is dependent on the characteristics of the structure (e.g., tissue) that individual x-ray photons pass through. Thus, if a patient is placed between the x-ray source 22 and the receptor 24, the variation in intensity of x-ray photons striking the receptor 24 gives an indication of the internal anatomic structure of the patient. The results are most often presented in the form of an image that maps the intensity of x-rays falling on various parts of the receptor 24 and thereby gives an indication of the distribution of tissue attenuation values through the different parts that the x-ray beams have passed.

Figure 1C:
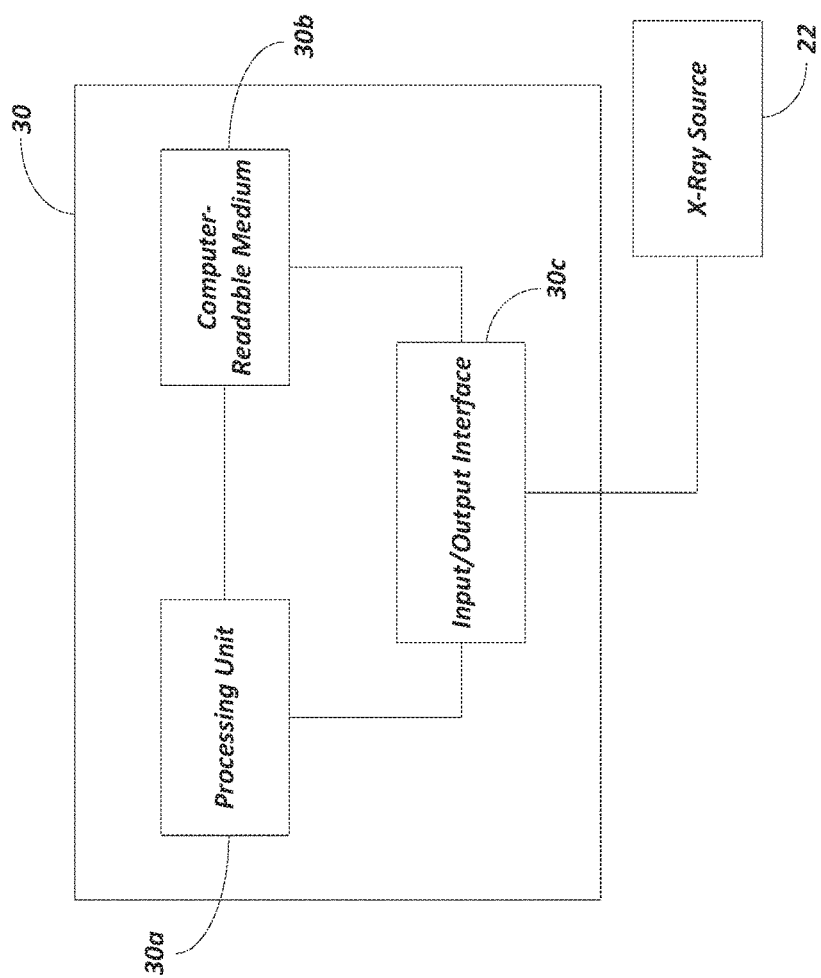
FIG. 1C schematically illustrates an x-ray source controller included in the system of FIG. 1A.

The controller 30 is configured to control the x-ray source 22. As illustrated in FIG. 1C, the controller 30 includes a processing unit 30a (e.g., a microprocessor), one or more non-transitory memory module(s) 30b, i.e., computer readable medium 30b and an input/output interface 30c. It should be understood, however, that in other constructions, the controller 30 includes additional, fewer, or different components.

The processing unit 30a is configured to retrieve instructions and data from the medium 30b and execute, among other things, instructions to control the x-ray source 22, the motion of the gantry 18, and the position (e.g., orientation) of the x-ray receptor 24. In some embodiments, as described in more detail below, the processing unit 30a is configured to retrieve instructions and data from the medium 30b and execute the instructions to control the x-ray source 22 to generate x-ray radiation at least two different energy levels. It should be understood that the x-ray source 22 and the controller 30 are sometimes referred to as a combined component. Therefore, it should be understood that functionality of the "x-ray source" described herein can be performed by the controller 30, the x-ray source 22, or a combination thereof.

The input/output interface 30c transmits data from the processor 30a to external systems, networks, and/or devices and receives data from external systems, networks, and/or devices. In particular, the input/output interface 30c communicates with the x-ray source 22. In some embodiments, the input/output interface 30c also communicates with the host computer 14. The input/output interface 30c can also store data received from external sources to the medium 30b and/or provide the data to the processor 30a.

X-ray images are either two-dimensional or three-dimensional. In two-dimensional images, all the information along the path of the x-ray has been combined into a single image. In three dimensional images, techniques associated with computed tomography ("CT") imaging are used to produce a volume dataset. Two dimensional images may be further divided into radiographs, in which all anatomy along the beam is equally in focus, or tomography, in which techniques are used to blur all parts of the anatomy except anatomy in a plane of a defined thickness perpendicular to the path of x-rays. Tomography is accomplished by moving the x-ray source 22 and x-ray receptor 24 in directions opposite to each other to cause motion blurring in all but one plane. The location of the plane can be controlled by controlling the relative motions of the source and the receptor, and the clocking speed of the TDI detector. In a frame-based, panoramic system, the parameters used in the tomosynthesis of the frame data can also be used to control the location of the plane.

Figure 2:
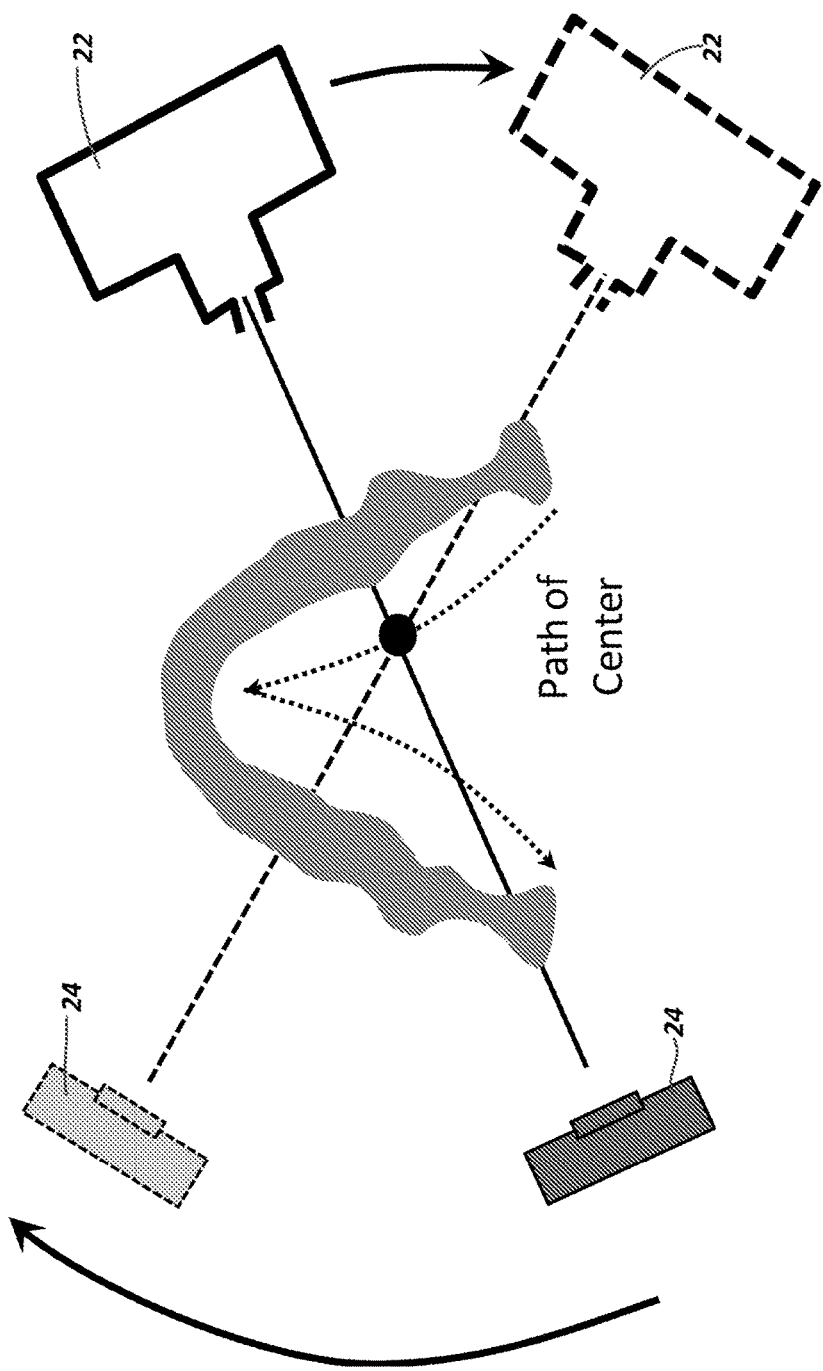
FIG. 2 schematically illustrates a path followed by a gantry included in the multi-spectral panoramic imaging system of FIG. 1A.

The imaging apparatus 11 is configured to perform panoramic imaging, a particular kind of tomographic imaging often used in dentistry. In this case, as illustrated in FIG. 2, the x-ray source 22 and the receptor 24 each follow a particularly defined path such that a curved plane that is centered on the patient's teeth is produced. The result is an image in which the patient's teeth and associated anatomy are in focus and other anatomy is blurred. A typical dental panoramic image might be, by way of example, 1200 pixels wide by 500 pixels high.

In one embodiment, a panoramic image can be formed by acquiring a sequence of projection frames, typically with dimensions of 16 to 60 pixels wide by 500 to 2,000 pixels high. A typical panoramic image requires the acquisition of approximately 1,000 to 3,000 frames over a period of approximately five to ten seconds. The panoramic image is then formed by combining the frames doing a sequence of horizontal shifts of the vertical lines, with interpolations and additions as is generally understood in art. A full panoramic scan is completed when sufficient projection frames are obtained from the x-ray receptor 24 to generate a panoramic image in which all of a patient's teeth are visible.

The imaging apparatus 11 applies the principles of multi-spectral imaging to panoramic imaging. As noted above, the attenuation of x-rays by a particular tissue type depends on the density of the tissue. However, the relative x-ray attenuation of two different tissue types also depends on the energy of the x-rays, which is usually expressed in kilovolts ("kV"). As is generally understood, x-ray sources emit x-ray radiation within a defined spectral band or spectrum and the stated "energy" or "energy level" rating of an x-ray source often refers to the highest energy level of the spectrum of the device. In this written description, the term "energy" is sometimes used without qualification. Such use is a shorthand expression and it should be understood that the reference to an energy or energy level is, unless the context indicates otherwise, not necessarily intended to refer to a single or monotonic energy. Rather, in most of the examples herein, a highest energy of an energy spectrum or band is being referred to. Furthermore, where an energy spectrum or spectral characteristic of an x-ray source is referred to herein, no particular implication is intended regarding the breadth or narrowness of the spectrum. For example, a spectrum can be broad or narrow, or in some cases can even be a single, sharp energy peak.

If x-ray images are acquired using two or more different x-ray energies or energy distributions, and the images are combined in some way—e.g., by subtraction—the results provide additional information beyond that which can be obtained with a single energy x-ray acquisition. Multiple energy acquisition is often referred to as dual energy or dual spectrum if two and only two energy spectra are involved. "Multi-spectral" is a generic term that refers to any case where more than one energy spectrum is used, but the term is sometimes used to refer to cases where three or more energy spectra are involved. Multi-spectral imaging can be used to increase image contrast in soft tissues and to more accurately make quantitative tissue measurements—e.g., bone density measurements. To provide such benefits, however, the multiple acquisitions need to be of the same anatomy. Therefore, there must be very little patient movement during the acquisition process. The imaging apparatus 11 uses principles of multi-spectral imaging to acquire acquisitions at different energy levels quickly where the time between acquisitions is insignificant as compared to patient motion. Accordingly, the imaging apparatus 11 can apply the principles of multi-spectral imaging to panoramic imaging to provide improved tissue contrast and more accurate tissue density evaluation.

In one embodiment, to perform multi energy acquisition, two or more sequential projection frames can be acquired at successive gantry positions or indices, where each of the frames at each index has an x-ray spectrum (e.g., x-ray energy) different from that of the preceding frame. Accordingly, in one embodiment, the x-ray source 22 (under the control of the controller 30) can alternate between two or more energy levels or spectra while acquiring sequential projection frames for the panoramic image. As noted above, a typical panoramic image requires the acquisition of approximately 1,000 to 3,000 frames over a period of approximately five to twenty seconds. Accordingly, to perform dual-energy acquisition, the x-ray source 22 would typically be switched at a rate of approximately 100 to 400 times per second. Current x-ray generation technology uses a heated filament in a cathode to generate electrons that are then accelerated by a high voltage field between the cathode and an anode (i.e., a target). The high-voltage energy electrons interacting with the target produce x-rays. Finite time, however, is required to turn the electron stream on and off, either by heating and then cooling the cathode, by removing the cathode-anode voltage, or by switching or pulsing the grid voltage. During the time required to turn on and off the electron stream, the x-ray spectrum and/or the amount of x-ray radiation can be in a non-determinate state.

Accordingly, to provide faster switching and avoid non-determinate x-ray states, the x-ray source 22 can be a high-speed pulsed x-ray source or sources 22 and the controller 30 can be configured to control the x-ray source 22 to vary the energy spectrum during image acquisition using different targets, different filtration, or different x-ray sources. The high-speed nature of such an x-ray source 22 allows for acquisition of lines at each gantry index with minimal gantry position shifts and patient motion, even though the gantry 18 is continuously moving during the acquisitions.

Figure 3A:
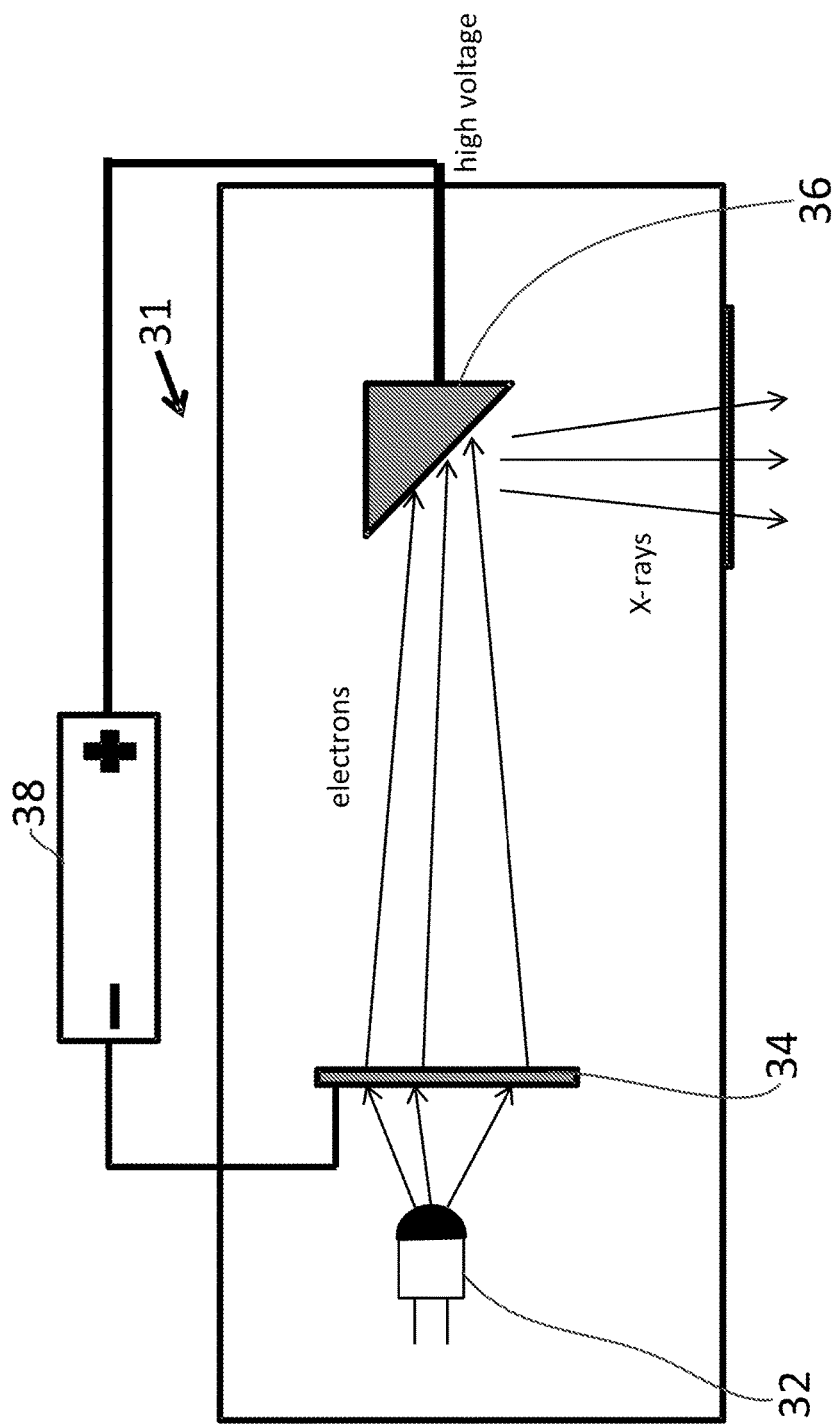
FIGS. 3A, 3B, and 3C schematically illustrate examples of radiation sources that can be included in the multi-spectral panoramic imaging system of FIG. 1A.

FIG. 3A illustrates one embodiment of a high-speed switching x-ray source 31. The high-speed switching x-ray source 31 includes an ultraviolet ("UV") light source 32 (e.g., a light emitting diode ("LED")), a cathode 34, an anode 36, and a high-voltage source 38. The high-voltage source 38 applies a voltage (e.g., a potential) between the cathode 34 and the anode 36. The UV light source 32 emits photons to the cathode 34, which optionally can be a cold cathode (e.g., a photocathode coated micro-channel plate). The cathode 34 converts the photons to an electron stream. The electron stream is accelerated by the voltage applied between the cathode 34 and the anode 36 by the high-voltage source 38. The electron stream travels from the cathode 34 to the anode 36. The electron stream then interacts with the anode 36 to produce (e.g., emit) x-rays or x-ray radiation. Different embodiments and variations of the high-speed switching x-ray source 31 are described below. However, the general functionality of the x-ray source 31 remains the same.

Within the high-speed switching x-ray source 31, the electron stream can be turned on and off quickly (e.g., in nanoseconds). Accordingly, the x-ray source 31 can be activated and deactivated quickly also. Typically, the high-voltage source 38 is a floating voltage source that is connected between the cathode 34 and the anode 36 to apply a voltage (e.g., a potential) between the cathode 34 and the anode 36. However, the high-voltage source 38 need not be floating—e.g., either terminal of the voltage source may be grounded. It should be understood that although the controller 30 is not illustrated in FIG. 3 or other figures illustrating the source 31, the high-speed switching x-ray source 31 is controlled by the controller 30.

Since the x-ray source 31 can be activated and deactivated quickly, the high-voltage source 38 can apply different voltages between the cathode 34 and the anode 36, which allows the x-ray source 31 to perform an interleaved multi-spectral panoramic image acquisition. For example, during a first time period, the x-ray source 31 is activated (i.e., the light source 32 can be turned on for a set time), and a first voltage is applied between the cathode 34 and the anode 36. Thus, during the first time period, the x-ray source 31 outputs x-ray radiation having a first energy characteristic (e.g., x-ray radiation of a first energy spectrum). Then, the x-ray source 31 is deactivated for a specified time period. During a second time period, the x-ray source 31 is activated again and a second voltage is applied between the cathode 34 and the anode 36. Thus, during the second time period, the x-ray source 31 outputs x-ray radiation having a second energy characteristic (e.g., x-ray radiation of a second energy spectrum). This cycle (e.g., activating and deactivating the x-ray source 31 to produce x-ray radiation of more than one energy spectrum) can be repeated for the acquisition of each line of the panoramic image until a full scan is completed.

Figure 4:
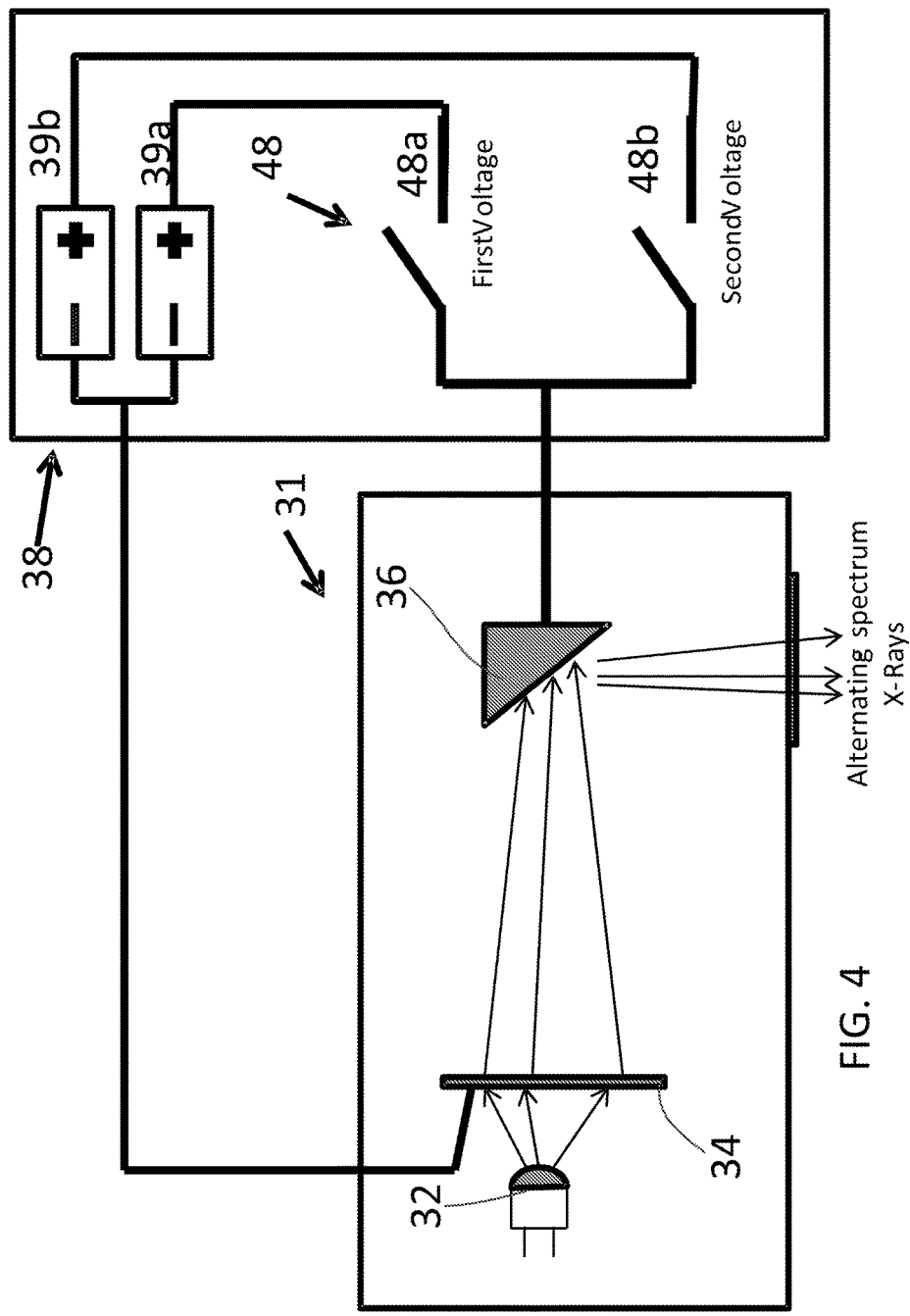
FIG. 4 schematically illustrates a plurality of voltage sources for the high-speed switching radiation source of FIG. 3.

For example, as illustrated in FIG. 4, to apply the first voltage and the second voltage between the cathode 34 and the anode 36 and, thus, generate two different x-ray energies, the high-voltage source 38 can include a set of switches 48 having a first high-voltage switch 48a and a second high-voltage switch 48b to selectively apply two different voltages or potentials to the anode 36. In the illustrated embodiment, the high-voltage source 38 includes a first voltage source 39a and a second voltage source 39b. The switches 48 then couple the anode 36 to one of the first voltage source 39a and the second voltage source 39b. In the illustrated embodiment, when the first high-voltage switch 48a is closed, the anode 36 is coupled to the first voltage source 39a. When the anode 36 is coupled to the first voltage source 39a, the x-ray source 31 outputs x-ray radiation having a first energy characteristic (e.g., x-ray radiation of a first energy spectrum). When the second high-voltage switch 48b is closed, the anode 36 is coupled to the second voltage source 39b. When the anode 36 is coupled to the second voltage source 39b, the x-ray source 31 outputs x-ray radiation having a second energy characteristic (e.g., x-ray radiation of a second energy spectrum). Optionally, the electron stream is turned off (e.g., the x-ray source 31 is deactivated) during the time that it takes for the first high-voltage switch 48a to open and the second high-voltage switch 48b to close (and vice versa). Optionally, the electron stream need not be turned off, but can just be left on for all or part of the panoramic scan. Either way, the cycle (e.g., coupling the anode 36 to one of the first voltage source 39a and the second voltage source 39b) is then repeated for each pair of projection frames.

Figure 5:
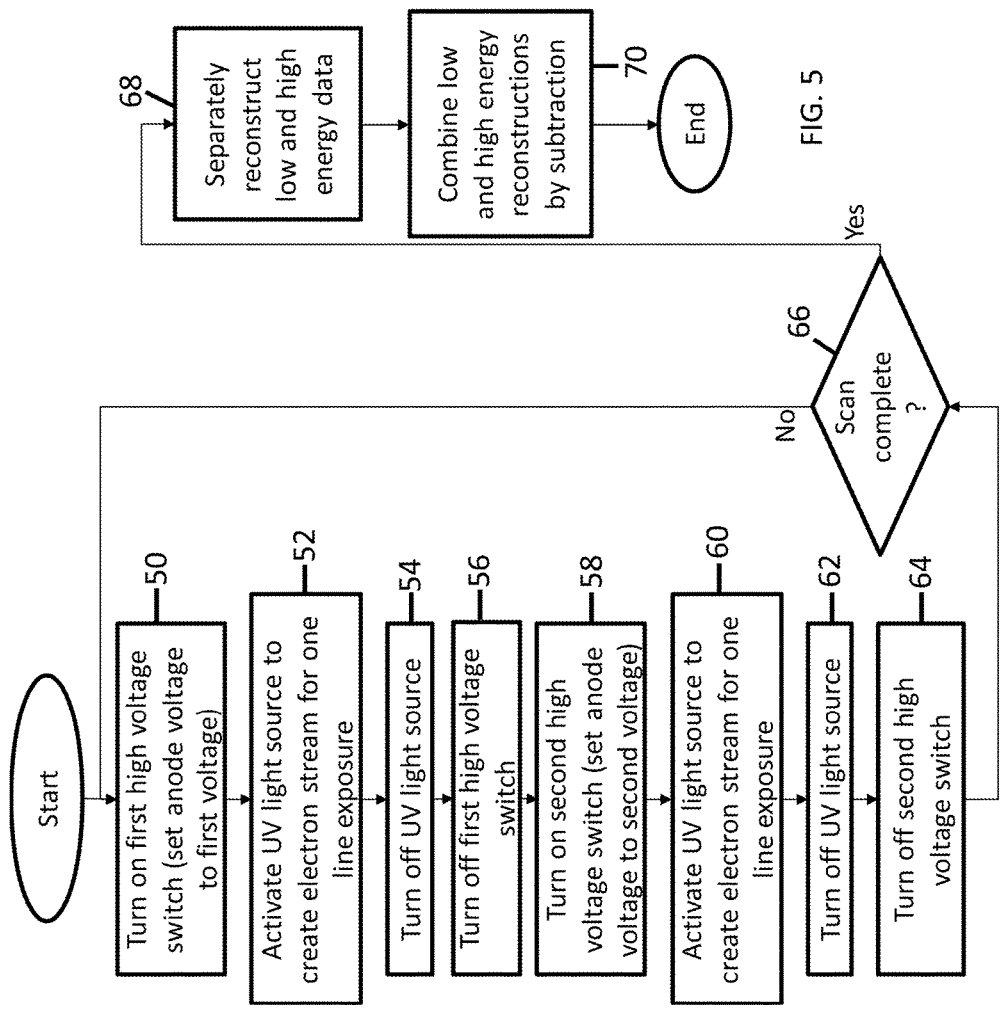
FIG. 5 is a flow chart illustrating a method of switching the anode voltage of the high-speed radiation source of FIG. 4.

In particular, FIG. 5 is a flow chart illustrating a method of operating the x-ray source 31 to create multi-spectral panoramic scans using the set of switches 48 connected to the anode 36. As illustrated in FIG. 5, as the scan begins, the first high voltage switch 48a is closed and the anode 36 is set to a first voltage (at block 50). The UV light source 32 is then activated to create the electron stream for a time equal to the exposure needed to create projection frame line (at block 52). After the line has been created, the UV light source 32 is turned off (at block 54), and the first high voltage switch 48a is reopened (at block 56). Sequentially, the second high voltage switch 48b is then closed and the anode 36 is set to a second voltage (at block 58). The UV light source 32 is turned on again for the same amount of time (at block 60) and thereafter turned off (at block 62). The second high voltage switch 48b is then reopened (at block 64). If the scan is not yet complete (at block 66), the first high voltage switch 48a re-closes (at block 50) and the process repeats until the scan is complete. Once the scan is completed, the first energy data and the second energy data (i.e., the high energy and low energy data) are reconstructed separately by the host computer 14 (at block 68). The host computer 14 then combines the separate reconstructions (e.g., by subtraction) (at block 70).

Figure 3B:
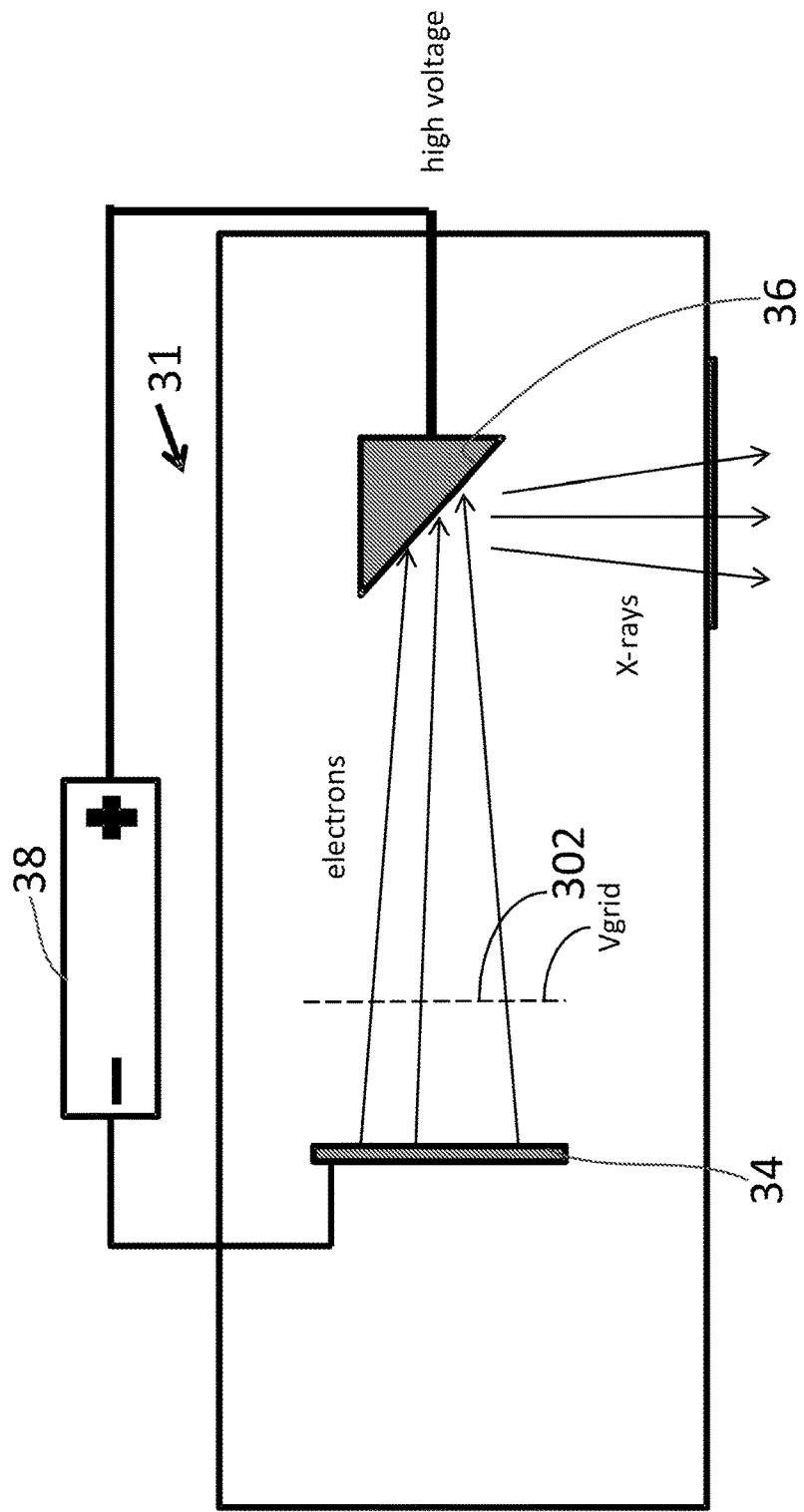

Optionally, the invention can be practiced using a hot-cathode x-ray source 31, as illustrated in FIG. 3B. In the source shown in FIG. 3B, the cathode 34 is heated to a temperature sufficient to generate free electrons. Since the electrons are thermally generated, the light source 32 illustrated in FIG. 3A can optionally be omitted from the x-ray source 31 illustrated in FIG. 3B. In addition, the x-ray source 31 illustrated in FIG. 3B includes a grid 302, which can be used to turn on and off, and/or modulate, the stream of electrons accelerated from the cathode 34 to the anode 36. Control of the electron stream is accomplished, for example, by adjusting the grid voltage $V_{grid}$.

Figure 3C:
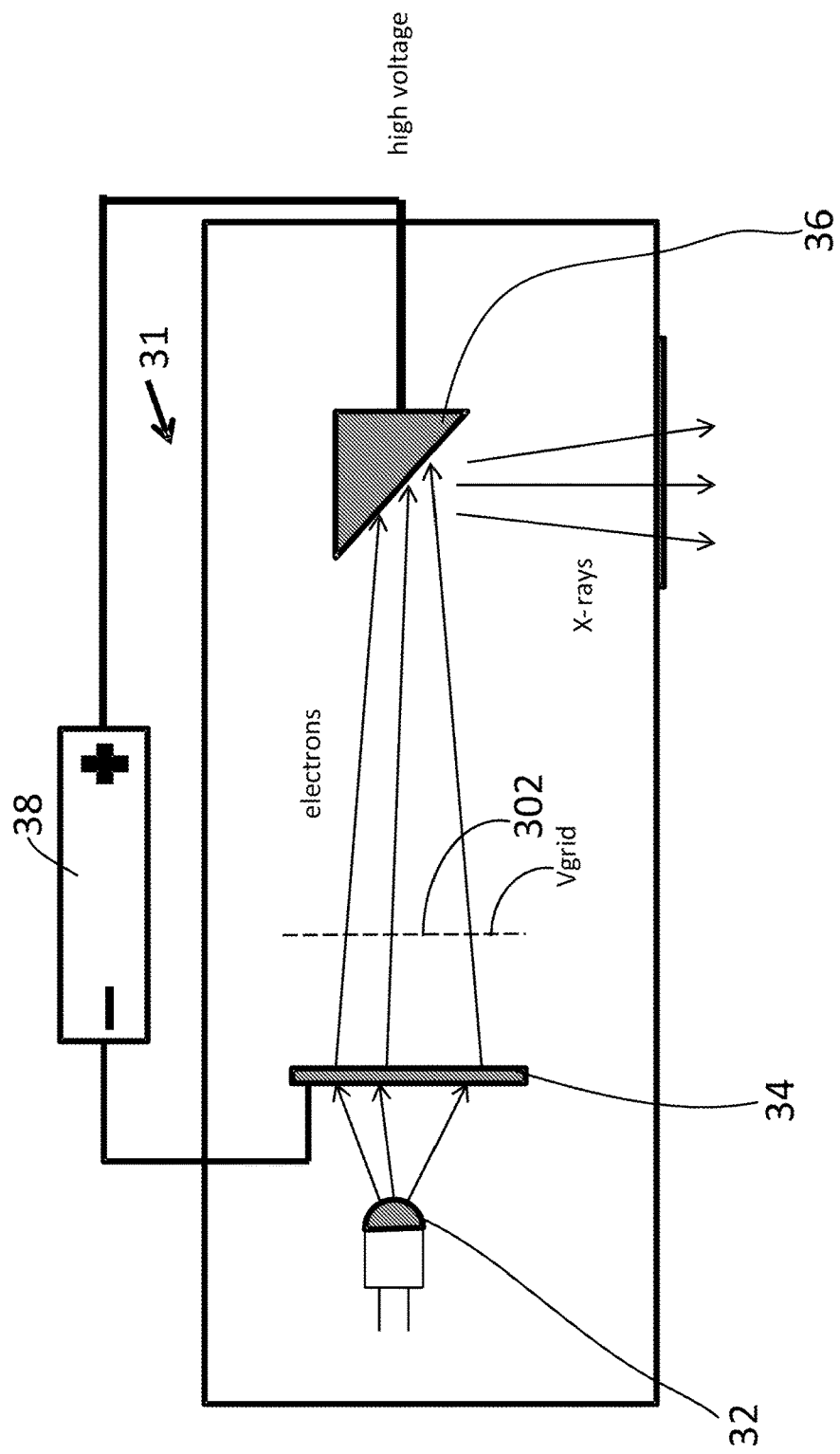

In addition, the invention can be practiced using an x-ray source 31 containing both a grid 302 and a light-activatable cathode 34 illuminated by a light source 32, as illustrated in FIG. 3C. Alternatively, or in addition, other kinds of hot or cold cathodes can be used. For example, the cathodes may include nanostructured material, for example, carbon nanotube cathodes.

Although for simplicity some of the drawings omit the light source 32 and/or the grid 302, it is to be understood that the various exemplary embodiments described herein can optionally be practiced with an x-ray source containing a grid 302, a light-activatable cathode 34 (illuminated by a light source 32), both, or neither.

Figure 6:
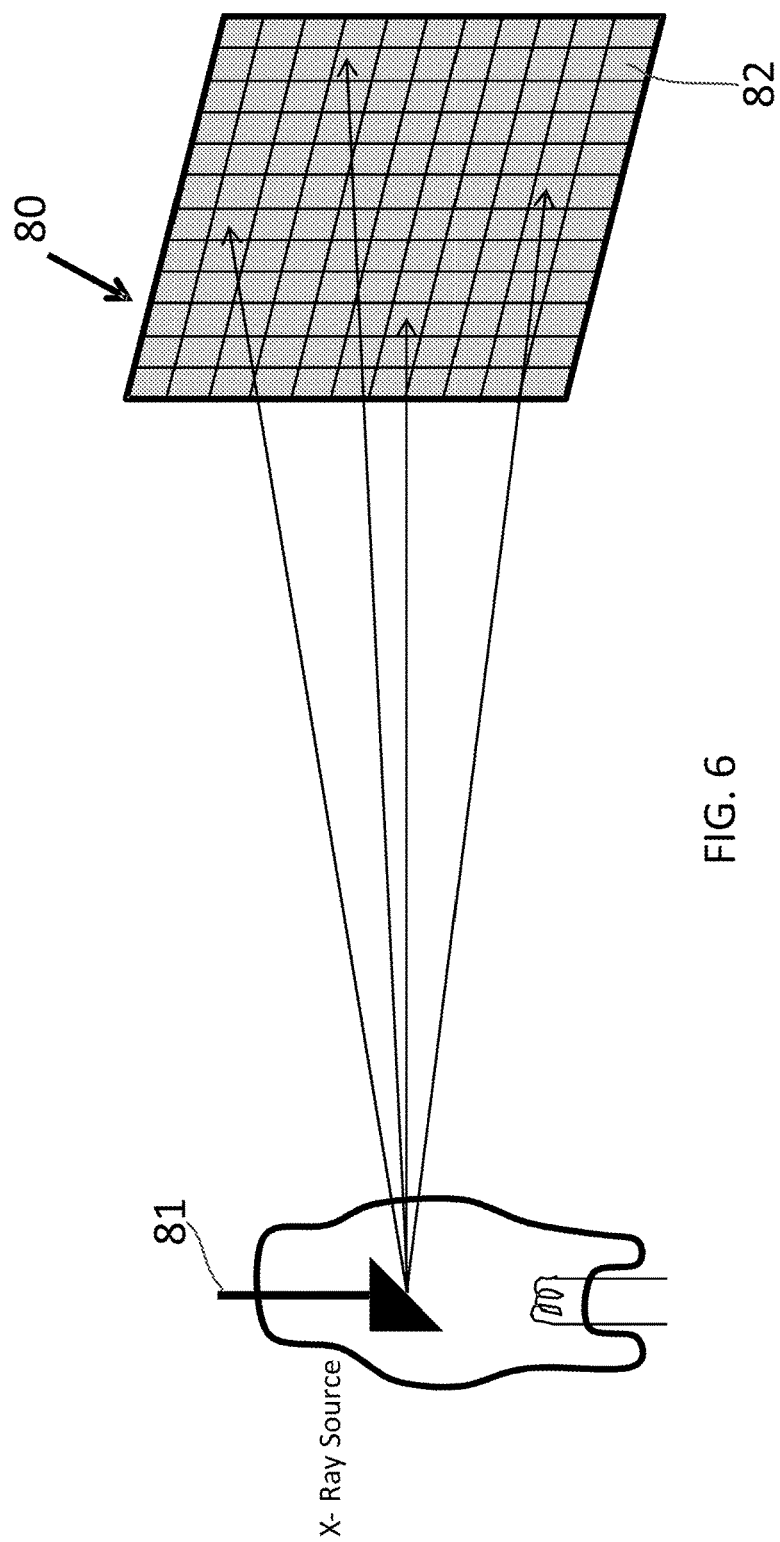
FIG. 6 schematically illustrates a radiation-energy-discriminating receptor panel.

Another embodiment of the invention uses a radiation-energy-discriminating detector panel 80 to create multispectral panoramic images. As illustrated in FIG. 6, a radiation source 81 generates radiation having a broad spectrum of energies (e.g., using a filament described above for traditional x-ray generation or a UV light as described above with respect to FIGS. 3-4). The total energy of the photons generated when the x-ray photon strikes a scintillator material on the radiation-energy-discriminating detector panel 80 is measured. The number of photons generated by a single x-ray photon is proportional to its energy. To provide rapid recovery between successive x-ray photons, which allows for these numbers to be determined, the radiation-energy-discriminating detector panel 80 includes more detector units 82 than a traditional receptor to constrain each radiation photon to a more localized area. The radiation-energy-discriminating detector panel 80 distinguishes, using the detector units 82, between x-ray radiation having a first energy and x-ray radiation having a second energy. Although the complexity and cost can be high for a radiation-energy-discriminating panel 80, the radiation-energy-discriminating panel 80 needed for panoramic dental imaging is narrow (e.g., wide enough to detect one linewidth of scan data), making a radiation-energy-discriminating detector 80 for panoramic imaging more practical.

Although the above description of the system in FIG. 6 has emphasized the use of an indirect-capture detector, which converts x-ray photons into lower-energy photons and then detects the lower-energy photons, the system can also use a direct-capture x-ray detector panel, which directly detects the x-ray photons with no need to convert them into lower-energy photons.

Figure 7A:
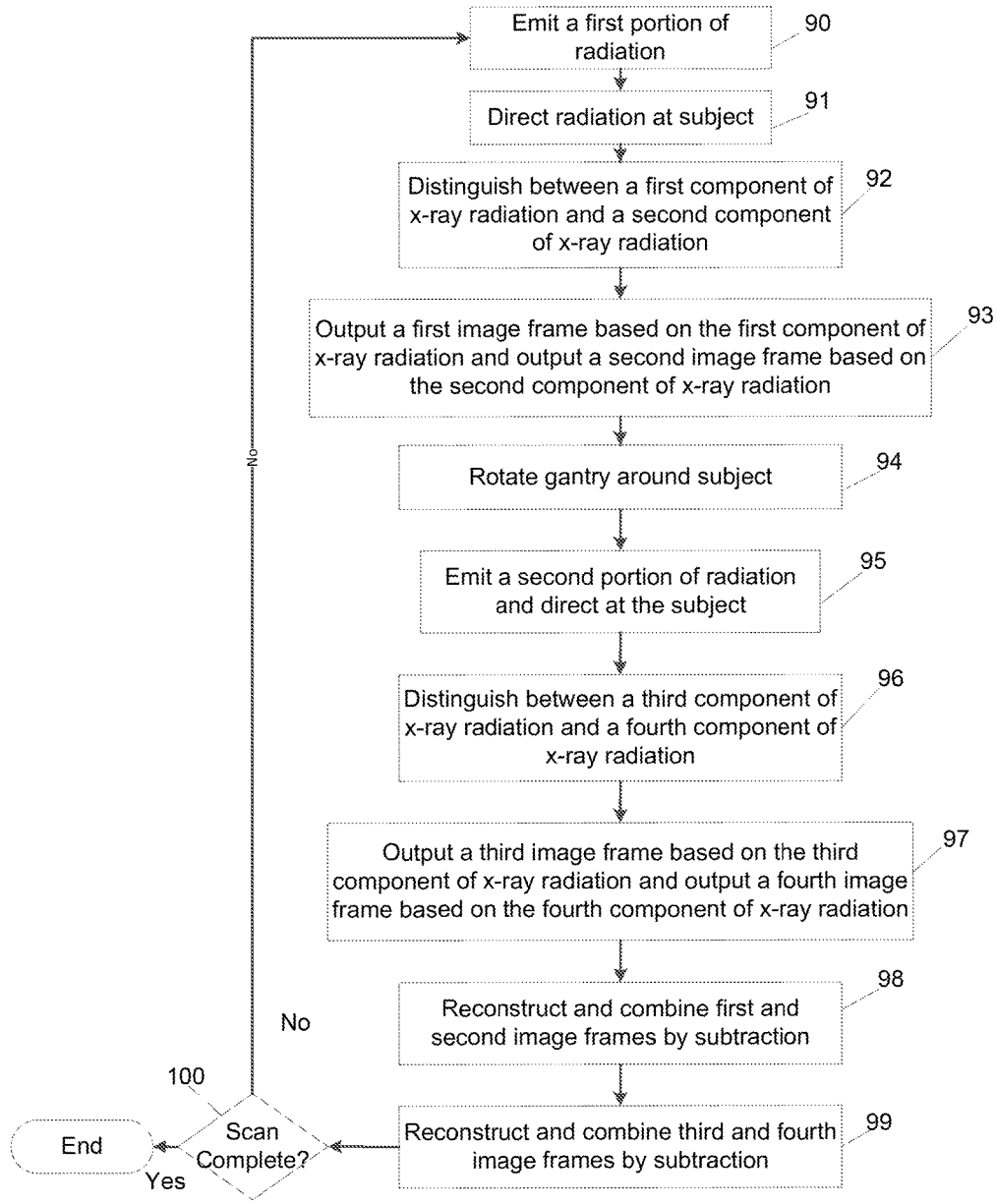
FIG. 7A is a flow chart illustrating operation of the radiation-energy-discriminating receptor panel of FIG. 6.

Accordingly, using the radiation-energy-discriminating detector 80, it is possible to produce an x-ray beam with a broad spectrum of energies and then divide (e.g., distinguish) the detected x-rays into two or more portions or "bins" of a plurality of energies. For example, FIG. 7A is a flow chart illustrating a method of using the radiation-energy-discriminating detector 80. As illustrated in FIG. 7A, the x-ray source 81 emits a first portion of radiation having a plurality of different energy levels (at block 90) and the radiation is directed at a subject (e.g., a patient) at block 91. The detector 80 distinguishes between a first component of x-ray radiation having a first energy and a second component of x-ray radiation having a second energy (block 92). A first image frame is outputted based on the first component of x-ray radiation (block 93) and a second image frame is outputted based on the second component of x-ray radiation (block 93). The gantry 18 changes angular position (block 94). The x-ray source 81 emits a second portion of radiation having a plurality of different energy levels—but optionally, having an energy spectrum similar or identical to that of the first portion of radiation—and directs it at the subject (block 95). The detector 80 distinguishes between a third component of x-ray radiation having the first energy and a fourth component of x-ray radiation having the second energy (block 96). A third image frame is outputted based on the third component of x-ray radiation (block 97) and a fourth image frame is outputted based on the fourth component of x-ray radiation (block 97). The first image frame and the second image frame are combined and reconstructed by subtraction (block 98), and the third image frame and the fourth image frame are combined and reconstructed by subtraction (block 99). If the scan is complete (block 100), the x-ray source is deactivated, and if the scan is not complete, the cycle is repeated.

Figure 7B:
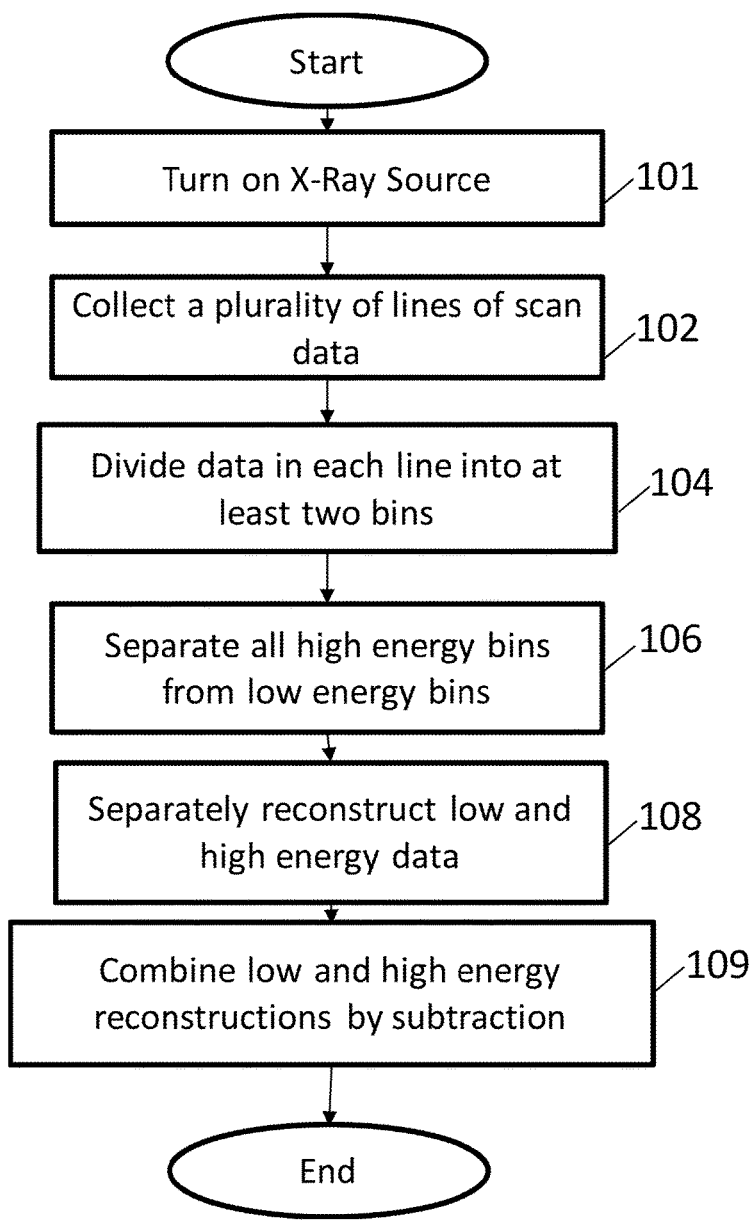
FIG. 7B is a flow chart illustrating an alternative operation of the radiation-energy-discriminating receptor panel of FIG. 6.

FIG. 7B illustrates an additional method for using the radiation-energy-discriminating detector 80. The x-ray source 81 emits x-ray radiation with a broad spectrum of energies (block 101), and the radiation-energy-discriminating detector panel 80 detects a plurality of lines of scan data or data frames (at block 102). The host computer 14 acquires the data for each line or frame and divides the data into at least two bins (e.g., a high energy bin and a low energy bin) (at block 104). The high energy bins are then separated from the low energy bins (at block 106). The data in the high energy bins is then reconstructed separately from the data in the low energy bins by the host computer 14 (at block 108). The host computer 14 then combines the separately reconstructed data (e.g., by subtraction) (at block 109). Alternatively, or in addition, the host computer 14 can combine the high-energy data and the low-energy data (e.g., by subtraction) to produce a single reconstruction.

Figure 8:
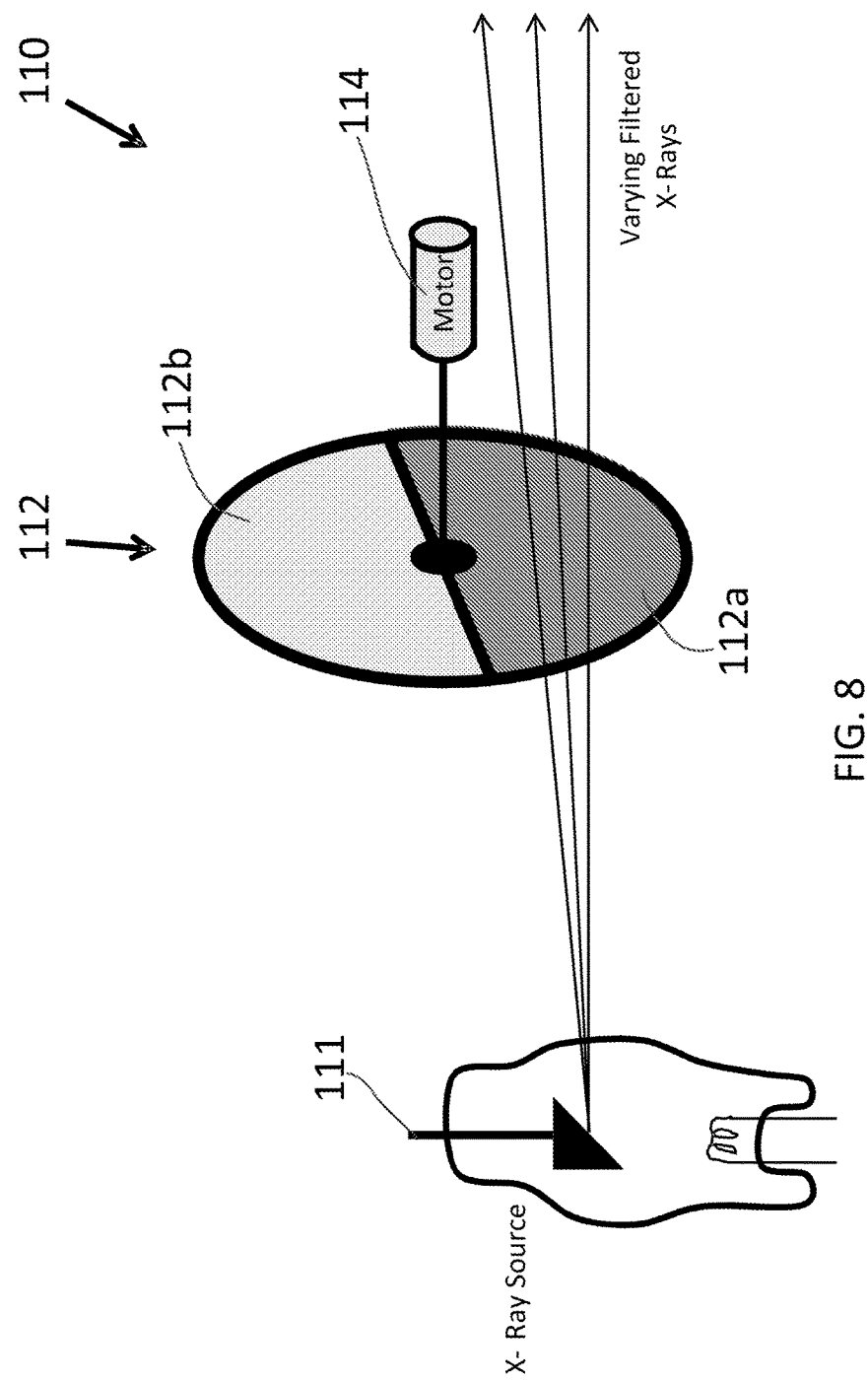
FIG. 8 schematically illustrates a rotating or, more generically, moving radiation filter.

FIG. 8 illustrates another embodiment of a radiation source 110 for performing multi-spectral imaging. As illustrated in FIG. 8, the radiation source 110 (e.g., an x-ray tube) can use an x-ray generation method using a filament described above for traditional x-ray generation or a UV light as described above with respect to FIGS. 3-4. The radiation source 110 also includes a moving or rotating radiation filter 112 coupled to a synchronized motor 114. The rotating radiation filter 112 includes a first filter portion and a second filter portion, which may be composed of two thin metal sheets. One half, the first filter portion, 112a of the sheet is made up of one type of material or a particular thickness of material, and the other half, the second filter portion, 112b is made up of a different type of material and/or a different thickness of material. Possible material types are copper, aluminum, a metal alloy, a sandwich of materials, or a thin film deposited on a substrate. For example, half 112a can be copper and half 112b can be aluminum. Alternatively, or in addition, half 112a can be thicker than half 112b, and/or one or both of the halves 112a and 112b can include at least one layer of copper and at least one layer of aluminum. Accordingly, the x-ray spectrum can be modified by positioning one of the first portion 112a and the second filter portion 112b of the filter 112 in front of an x-ray source 111, which has a wide spectrum of x-ray photon energies. The filter 112 can narrow the spectrum by eliminating a set of energy photons that are absorbed by one of the first filter portion 112a and the second filter portion 112b of the filter 112. Therefore, as the filter 112 moves (in this case, rotates) and a different half of the filter 112 is positioned in front of the x-ray source 111, the filter 112 absorbs (e.g., filters) a different set of energy photons, which creates a different narrowed spectrum of energy.

In one embodiment, the rotating radiation filter 112 is located outside of the radiation source 111. The radiation source 111 emits radiation having a spectrum with multiple energies, while the rotating radiation filter 112 is rotated by the synchronized motor 114 to turn at the same rate as the time needed for two or more acquisitions per line or frame. As the radiation beam passes through the rotating radiation filter 112, depending on the position of the filter 112 (i.e., which half 112a or 112b is positioned in front of the radiation beams), only a certain energy level of radiation will pass through the filter 112. Thus, the effect of the filter 112 is to create two radiation streams. One stream has a first energy level and the second has a different energy level.

Figure 9:
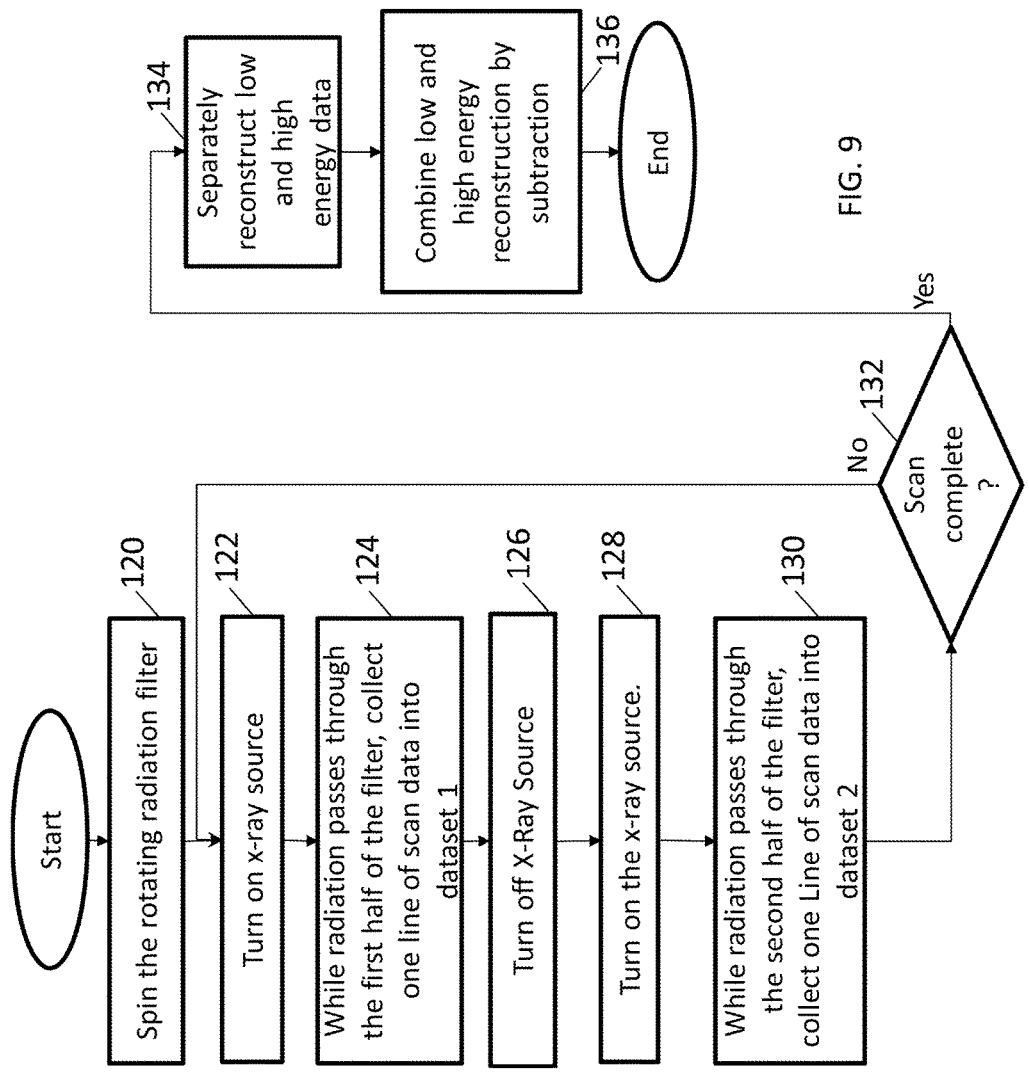
FIG. 9 is a flow chart illustrating operation of the moving radiation filter of FIG. 8.

For example, FIG. 9 illustrates a method of operating the rotating radiation filter 112. As illustrated in FIG. 9, at the beginning of the scan, the rotating radiation filter 112 begins spinning (at block 120) and the radiation source 111 is turned on (at block 122). While the radiation passes through the first half 112a of the filter 112, x-ray radiation having a first energy characteristic (e.g., x-ray radiation of a first energy spectrum) is detected by an x-ray receptor and the x-ray receptor collects data into a first dataset for projection frame of the scan (at block 124). Optionally, the x-ray source 111 is then turned off, or deactivated (at block 126). Although not essential in every system, turning off the x-ray source 111 during transition of the wheel eliminates a non-determinate state of radiation that otherwise may occur during the transition period, which has the advantage of reducing patient dose.

When the radiation begins passing through the other half 112b of the filter 112, the x-ray source is turned back on (at block 128) and x-ray radiation having a second energy characteristic (e.g., x-ray radiation of a second energy spectrum) is detected by the x-ray receptor and the x-ray receptor collects data into a second data set for the location of the scan at a different energy level (at block 130). The x-ray source 111 can then be turned off and the cycle repeats until the scan is complete (at block 132). After the scan is complete, the host computer 14 separately reconstructs the datasets (at block 134) and combines the reconstructions (e.g., by subtraction) (at block 136). While an approach of turning on and off the x-ray source might require a high-speed switching x-ray source, it is also possible to leave the x-ray on during the whole cycle. This would allow a standard x-ray source to be used.

It should be noted that in the embodiments described in FIGS. 7 and 9, low and high energy data can be separately reconstructed and then combined by subtraction. Combining high and low energy first and then performing reconstruction is also possible. There are also other ways than those specifically described to combine the high and low energy, whether it be done first or second.

Figure 10:
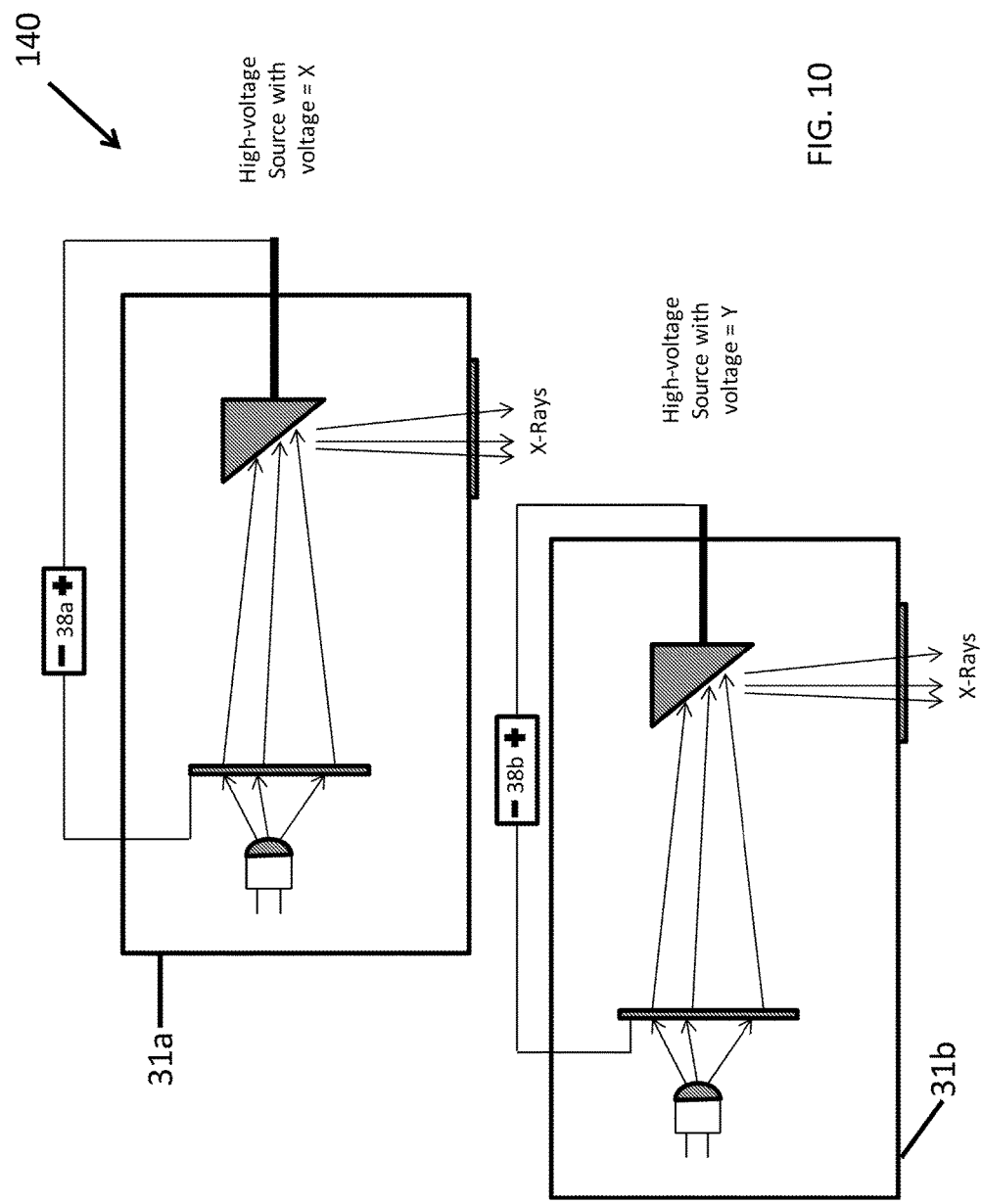
FIG. 10 schematically illustrates two radiation sources that operate at different voltages from each other.

There are other approaches for obtaining multi-spectral panoramic images. For example, FIG. 10 illustrates another embodiment of a high-speed switching x-ray source 140 that includes two separate high-speed switching x-ray sources, a first x-ray source 31a and a second x-ray source 31b as described above with respect to FIG. 3. Each of the x-ray sources 31a and 31b outputs x-rays at different energy levels (e.g., x-ray radiation having a first and second energy characteristic), because they are powered by high-voltage sources (38a and 38b, respectively) that produces different voltages (illustrated as X and Y, respectively). The first x-ray source 31a includes a first cathode and a first anode. The first high-voltage source 38a applies a first voltage to the first cathode (e.g., a ground voltage) and applies a second voltage to the first anode (e.g., a positive voltage). The second x-ray source 31b includes a second cathode and a second anode. The second high-voltage source 38b applies a third voltage to the second cathode (e.g., a ground voltage) and applies a fourth voltage to the second anode (e.g., a positive voltage). Both high-speed switching x-ray sources 31a and 31b would be located proximal to each other within the gantry 18. Geometry adjustments of the sources 31a and 31b or other components of the imaging apparatus 11 (e.g., the gantry or the receptor) could be made to make the outputs of the sources 31a and 31b as close as possible to each other (i.e., as if they originated from the same x-ray source). Software could also be used to adjust for the difference in position of the x-ray source 31 when processing the data collected from the scan (e.g., at the host computer 14).

Figure 11:
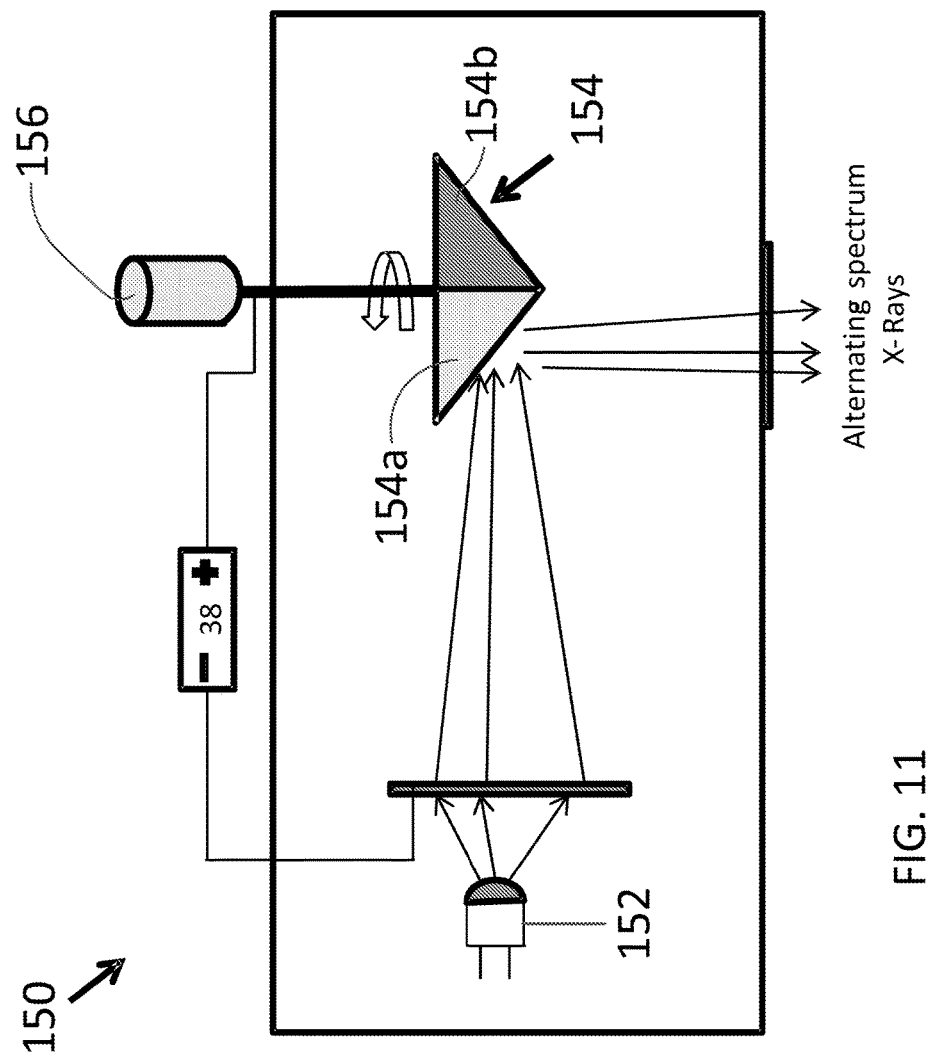
FIG. 11 schematically illustrates a high-speed radiation source that includes a single ultraviolet light source and a rotating or moving, two-component anode.

FIG. 11 illustrates yet another embodiment of a high-speed switching x-ray source 150. The source 150 includes a UV light source 152, a cathode, and a rotating, two-component anode 154. The rotating anode 154 includes two halves, a first section 154a and a second section 154b, and each section is made up of a different material that produces radiation with different spectra, for example, tungsten and copper. The rotating anode 154 is connected to a synchronized motor 156. The rotating anode 154 moves between a first position in which the first section 154a receives (interacts) with the electron stream emitted by the cathode, and a second position in which the second section 154b receives (interacts) with the electron stream emitted by the cathode. When the rotating anode 154 is in the first position, the x-ray source 150 produces x-ray radiation having a first energy characteristic (e.g., having a first energy spectrum), and when the rotating anode 154 is in the second position, the x-ray source 150 produces x-ray radiation having a second energy characteristic (e.g., having a second energy spectrum). The cathode may generate a first electron stream when the rotating anode 154 is in the first position, and generate a second electron stream when the rotating anode 154 is in the second position, so that the x-ray source 150 may generate x-ray radiation having at least a first energy characteristic and a second energy characteristic. Optionally, but not necessarily, a high-speed switching light source 152 would be used to turn off the electrons during a transition period of the anode 154. Alternatively, or in addition, the electron stream can also be turned on and off using a grid (not shown), or by turning the cathode-anode voltage source 38 on and off. As yet another option, the electron stream can be left on. In some embodiments, the rotating anode 154 can operate similar to the rotating filter 112 described above with respect to FIG. 8.

Figure 12:
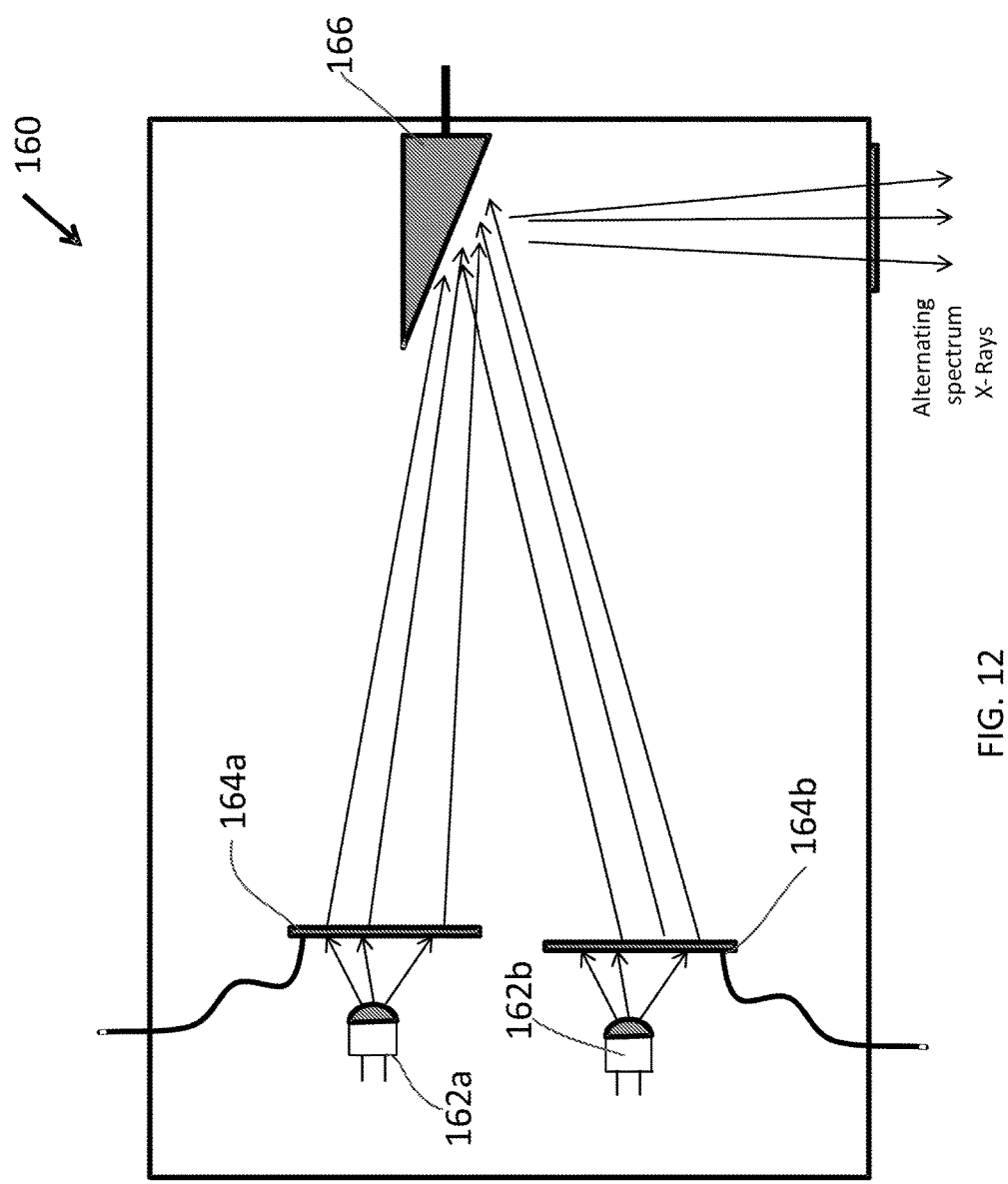
FIG. 12 schematically illustrates a high-speed radiation source that includes two ultraviolet light sources and a single anode, and each light source operates at different voltage from the other.

FIG. 12 also illustrates another embodiment of a high-speed switching x-ray source 160. Optionally, but not necessarily, the source 160 includes two UV light sources 162a and 162b. Each light source is connected to a first cathode 164a and a second cathode 164b, respectively. The first cathode 164a is coupled to a first voltage source (not shown) that applies a first voltage to the first cathode 164a. The second cathode 164b is coupled to a second voltage source (not shown) that applies a second voltage to the second cathode 164b. The second voltage is different than the first voltage. Optionally, during operation, the UV light sources 162a and 162b can be alternatingly turned on and off, with only one source emitting light at a time. Alternatively, or in addition, the electron beams can also be turned on and off using one or more grids (not shown), or by turning the cathode-anode voltage on and off. Either way, a single common anode 166 receives the electron beams emitted from one of the first cathode 164a and the second cathode 164b, and converts the beams into radiation beams of different spectra according to the voltages applied at the two cathodes 164a and 164b. Because only one light source is turned on at one time, the anode 166 only receives one electron beam at one energy level at a time. Accordingly, energy spectrum change occurs by turning off one electron source and turning on the other.

Figure 13:
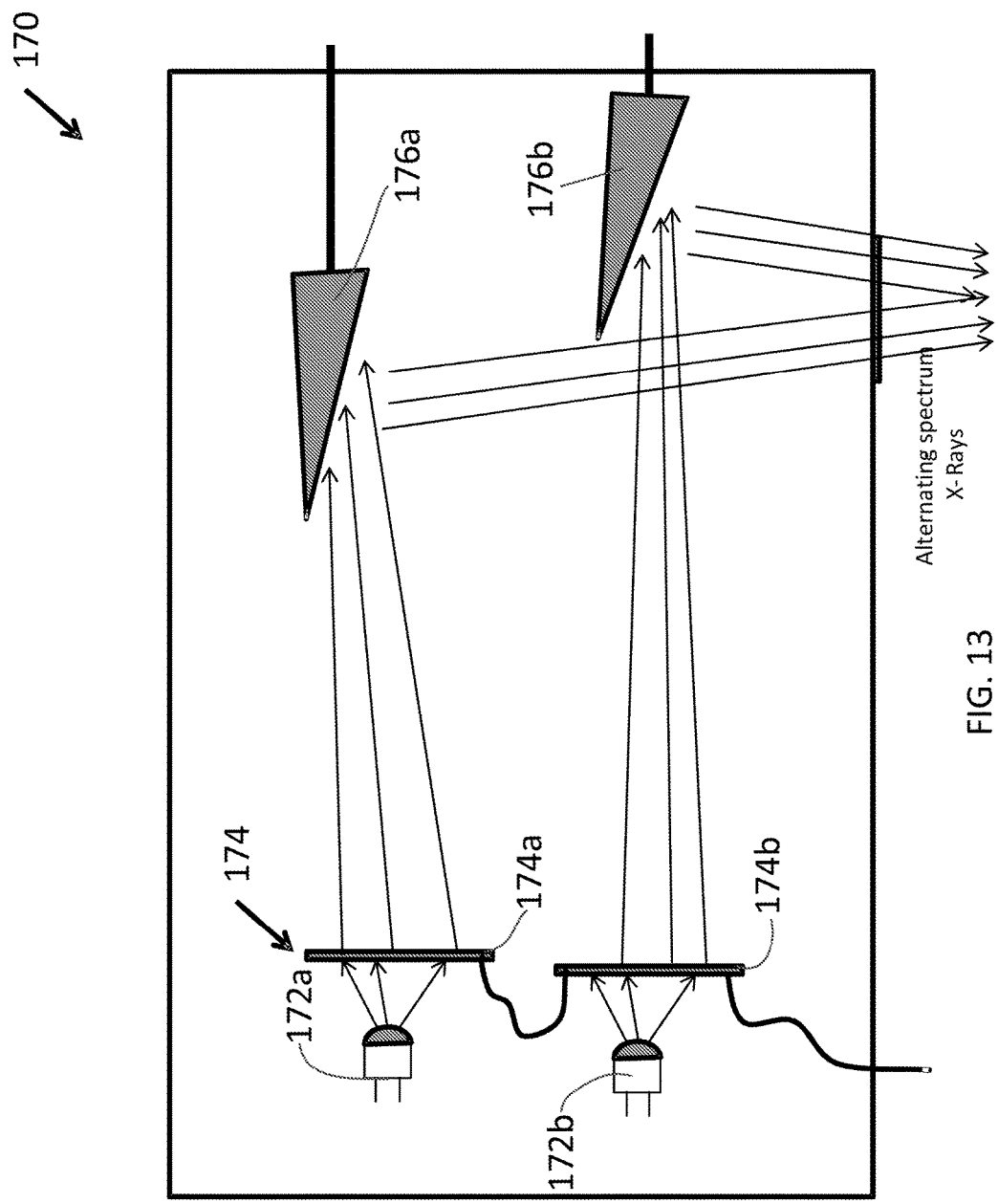
FIG. 13 schematically illustrates a high-speed radiation source including two ultraviolet light sources that operate at two different voltages and two anodes that operate at different voltages.

FIG. 13 illustrates another embodiment of a high-speed switching x-ray source 170. As illustrated in FIG. 13, the source 170 includes two UV light sources 172a and 172b, a first cathode 174a and a second cathode 174b both at a single common first voltage, a first anode 176a and a second anode 176b (e.g., contained within a single vacuum tube envelope). A second voltage, different than the first voltage, is applied to the first anode 176a, and a third voltage, different than the first voltage and the second voltage, is applied to the second anode 176b. Each UV light source 172a and 172b causes the respective cathode 174 to generate an electron beam that accelerates to and interacts with the respective anode 176a and 176b, which each generate radiation at a particular energy level. During operation, the UV light sources 172a and 172b are alternatingly turned on one at a time, which produces radiation of one energy level at a time. Therefore, the source 170 includes two high-speed switching electron sources 172a, 172b and two targets 176a, 176b, with the cathodes 174a, 174b at the same potential but the targets 176a, 176b at different potentials. For example, when the first UV light source 172a is activated, the first cathode 174a generates an electron beam that interacts with the first anode 176a to generate x-ray radiation having a first energy characteristic (e.g., a first energy spectrum). When the second UV light source 172b is activated, the second cathode 174b generates an electron beam that interacts with the second anode 176b, to generate x-ray radiation having a second energy characteristic (e.g., a second energy spectrum). Alternatively, or in addition, the different energy levels of the respective anodes 176a and 176b can be achieved by using anodes made of different materials—e.g., one from tungsten and one from copper. Accordingly, energy spectrum change occurs by turning on one electron source and turning off the other electron source. Furthermore, the use of light-activatable cathodes to turn the beams on and off is optional. For example, the electron beams can also be turned on and off using one or more grids (not shown), or by turning the cathode-anode voltages on and off, or the beams can be left on.

Figure 14:
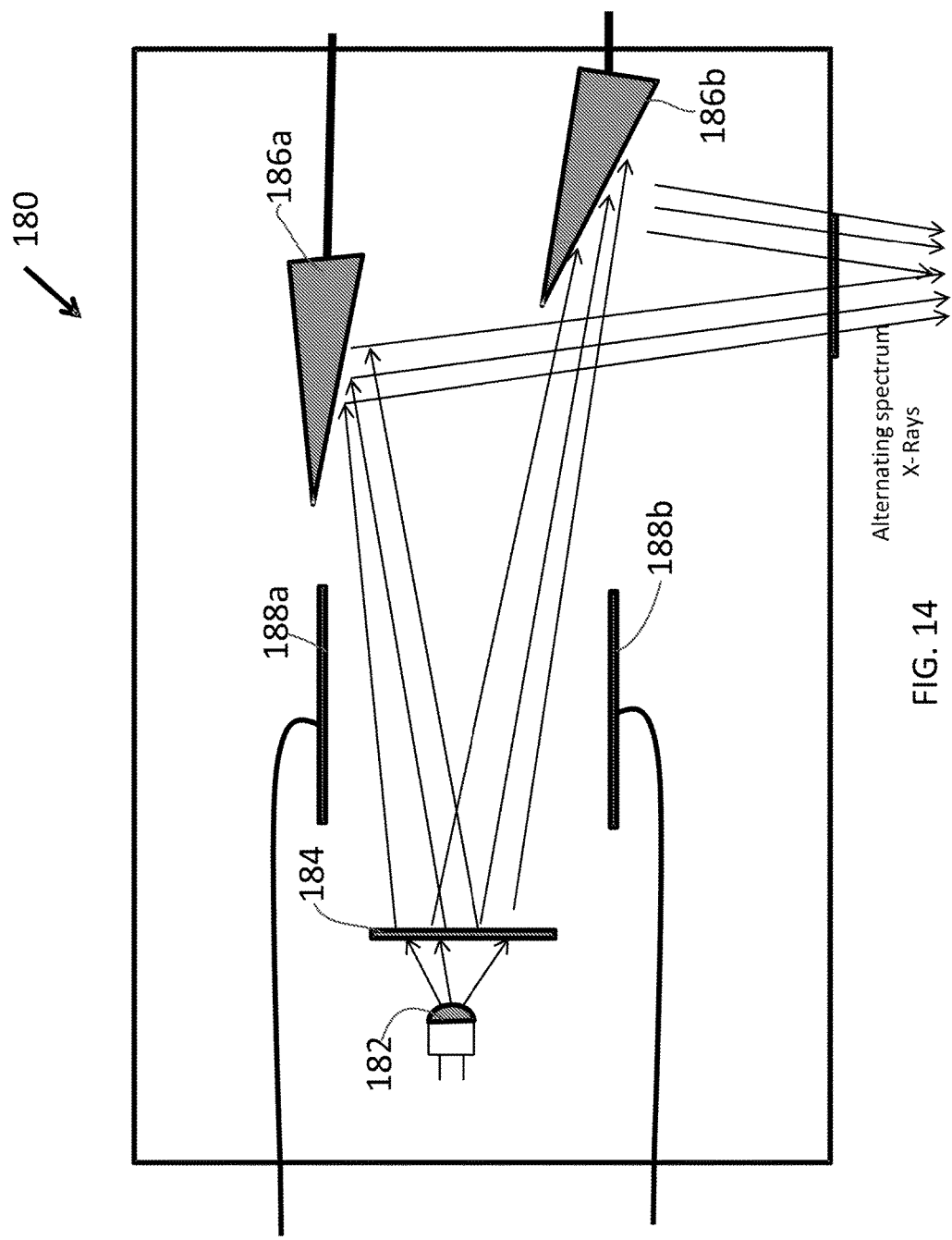
FIG. 14 schematically illustrates a high-speed radiation source including a single ultraviolet light source with two anodes at that operate at different voltages and a set of electron-steering electrodes.

FIG. 14 illustrates a further embodiment of a high-speed switching x-ray source 180. The source 180 includes a high-speed switching electron source or UV light source 182, a cathode 184 at a first voltage, a first anode 186a at a second voltage, a second anode 186b at a third voltage, a first electron steering plate (or electron-deflecting electrode) 188a and a second electron-steering plate (or electron-deflecting electrode) 188b. The first and second anodes 186a, 186b are at two different voltages and/or are made of different materials. In the illustrated embodiment, the first and second electron-deflecting electrodes 188a, 188b are contained within a single vacuum tube envelope. The electron-deflecting plates or electrodes 188a and 188b can be given opposite charges and/or different voltages, thus creating an electric field between the electron-deflecting plates 188a, 188b to direct the electrons to one of the anodes 186a and 186b. The difference in voltage between the electron steering plates 188a, 188b is modulated, which guides the electron stream from the cathode 184 to the appropriate anode 186a, 186b. This can be done by changing the voltage on one or both of the plates 188a, 188b—e.g., (1) by alternatingly charging plate 188a (either negatively or positively) while grounding plate 188b, then charging plate 188b while grounding plate 188b, and so on, or (2) by alternatingly charging plate 188a negatively and plate 188b positively, then charging plate 188a positively and plate 188b negatively, and so on. For example, when the first electron-deflecting electrode 188a is at a higher voltage than the second electron-deflecting electrode 188b, the resulting, downward-oriented electric field guides the electron beam from the cathode 184 upward to the first anode 186a, since electrons are negatively charged. Thus, when the electron beam interacts with the first anode 186a, the x-ray source 180 generates x-ray radiation having a first energy characteristic (e.g., having a first energy spectrum). On the other hand, when the first electron-deflecting electrode 188a is at a lower voltage than the second electron-deflecting electrode 188b, the resulting, upward-oriented field guides the electron beam from the cathode 184 downward to the second anode 186b. Thus, when the electron beam interacts with (travels to) the second anode 186b, the x-ray source 180 generates x-ray radiation having a second energy characteristic, for example, having a second energy spectrum. In some embodiments, the UV light source 182 is turned off when the polarity of the steering plate field is being switched (e.g., when the voltage applied to each of the steering plates 188a, 188b is changed). As with the other embodiments described above, the use of light-activatable cathodes to turn the beams on and off is optional. For example, the electron beams can be left on, or they can be turned on and off using one or more grids (not shown), or by turning the cathode-anode voltages on and off.

Figure 15:
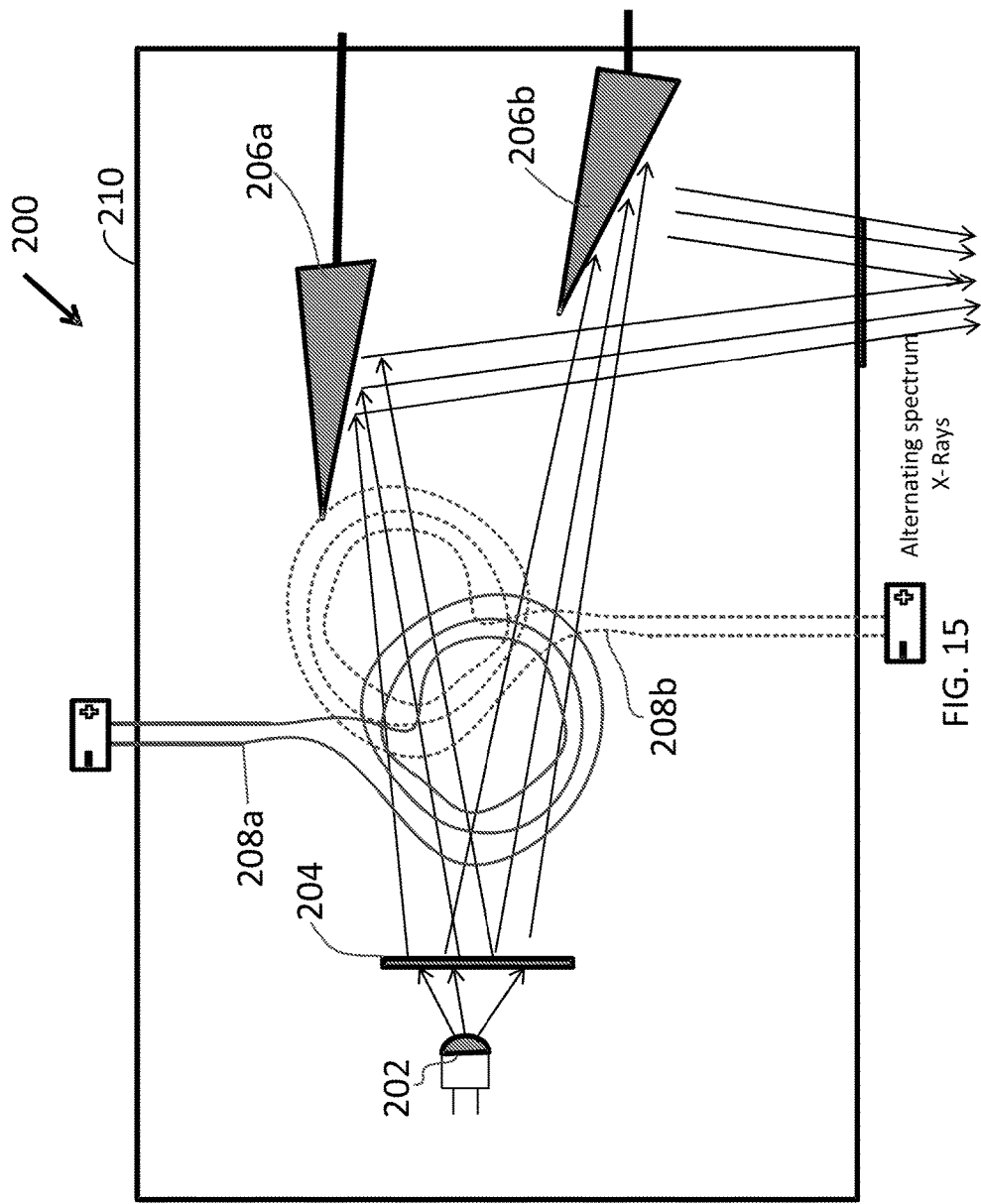
FIG. 15 schematically illustrates a high-speed radiation source including a single ultraviolet light source with two anodes that operate at different voltages and a set of steering magnets.

FIG. 15 illustrates another embodiment of the invention in the form of a high-speed switching x-ray source 200. The source 200 includes a UV light source 202, one cathode 204 at a first voltage (not shown), two anodes (a first anode 206a and a second anode 206b) at different voltages and/or made of different materials, and two steering magnets 208a and 208b. A second voltage (not shown), different than the first voltage, is applied to the first anode 206a and a third voltage, different than the first and second voltages, is applied to the second anode 206b. In the embodiment shown in FIG. 15, the magnets 208a and 208b are electromagnets and arranged in a dipole arrangement. Note that in FIG. 15, the magnets 208a and 208b appear to be slightly offset only to facilitate illustration of both magnets 208a, 208b. In some embodiments, the magnets 208a, 208b are aligned to generate an even magnetic field. Depending on the size of the source 200 and the magnets, the magnets may be positioned outside (as shown) or within a single vacuum tube envelope 210. The steering magnets 208a and 208b are activated to generate a magnetic field between them. The magnitude and/or the polarity of the current provided to magnets may be varied to change the strength of and the direction of the magnetic field. Changes in the direction and strength of the magnetic field can be used to guide the electrons to the appropriate anode 206a or 206b. In the illustrated embodiment, the magnets 208a, 208b are coils with an axis perpendicular to the page. Therefore, the magnetic field created between the magnets 208a, 208b is able to direct the electron beams either downward or upward to the first anode 206a or to the second anode 206b. When the electrons are guided to the first anode 206a, the x-ray source 200 generates x-ray radiation having a first energy characteristic (e.g., having a first energy spectrum) since the first anode 206a is at the second voltage, and when the electrons are guided to the second anode 206b, the x-ray source 200 generates x-ray radiation having a second energy characteristic (e.g., having a second energy spectrum) since the second anode 206b is at the third voltage. Instead of a dipole arrangement, other arrangements such as a quadrapole arrangement are possible.

Figure 16:
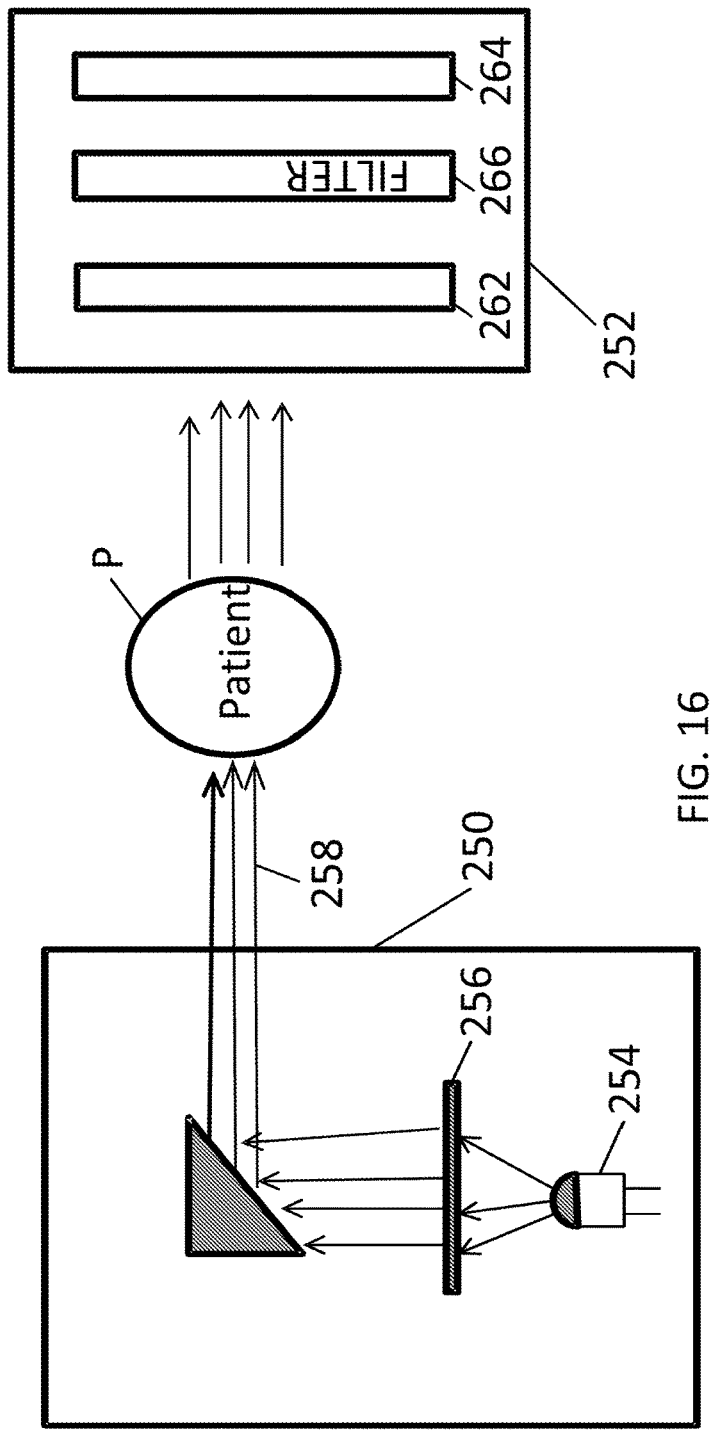
FIG. 16 schematically illustrates a broad spectrum radiation source and a multiple-detecting element detector.

FIG. 16 illustrates another embodiment of the invention that includes a broad-spectrum x-ray source 250 and a detector 252. The source 250 can include a UV light source 254, a cathode 256, and an anode (not shown). Alternatively, the source 250 can include other components to generate a broad-spectrum stream of x-ray radiation 258. During an imaging procedure, the x-ray radiation 258 is directed to a patient (or subject) or portion of a patient P. A portion of the radiation is absorbed by the patient P, and the remainder impinges upon the detector 252. The detector 252 includes a first detector element or receptor 262 and a second detector element or receptor 264. Optionally, the detector 252 includes a filter 266. The filter 266 may be a copper sheet or screen. Both high-energy and low energy photons in the portion of the stream that passes through the patient P are received by the first receptor 262. Higher energy photons pass through the first receptor 262 and the filter 266 and are received by the second receptor 264, whereas some of the lower-energy photons are blocked by the filter 266 and/or the first receptor 262. In other words, the first receptor 262 receives x-ray radiation having a first energy characteristic (e.g., having a first energy spectrum), and the second receptor 264 receives a second image frame based on x-ray radiation having a second energy characteristic (e.g., having a second energy spectrum with reduced lower-energy x-rays). The filter 266, when implemented, enhances the contrast between the image information acquired by the first receptor 262 and the image information acquired by the second receptor 264.

In contrast to certain other embodiments where multiple energy acquisition is achieved using an x-ray source that generates radiation in two or more relatively distinct spectra, in the embodiment disclosed in FIG. 16, the configuration of the detector is such that a broad-spectrum source may be used and multiple energy acquisition is achieved as the result of using multiple receptors, each of which receives radiation of a different energy spectra as a consequence of relatively low energy photons being absorbed in the first receptor 262 and/or the filter 266, and higher energy photons being absorbed by the second receptor 264.

As noted above, it is possible to achieve different absorption simply because low energy radiation will be absorbed by the first receptor 262 and/or the filter 266, while higher energy radiation will pass through the first receptor and be absorbed by the second receptor. However, if desired, a more particular approach may be taken by purposely designing the receptors with different types of scintillators to tune or adjust the absorption characteristics of each receptor.

Additional variations of the embodiments described above are also possible. For example, the fast-switching x-ray sources used in the embodiments described with respect to and illustrated in FIGS. 3, 4, and 10, may be replaced by other types of x-ray sources including x-ray sources with carbon nanotube-based cathodes including those available from Xintek, Inc. (http://www.xintek.com/products/xray/index.htm).

Thus, the invention provides, among other things, a radiation system that allows for multi-spectral panoramic scans to be obtained from a patient while keeping cost and time reasonable. It should be understood that multi-spectral imaging does not depend on entirely different energy spectra in the different acquisitions. Information can be gained from multi-spectral imaging even if the spectra of each acquisition overlap as long as the spectra are different. It should also be understood that although the x-ray sources described above are used to two acquisitions, the sources can be modified to perform more than two acquisitions. In particular, additional voltages, light sources, cathodes, and anodes can be used to generate more than two different energy spectra. Similarly, any of the rotating components described above can be configured with more than two different sections to generate more than two different energy spectra.

Various features and advantages of the invention are set forth in the following claims.

What is claimed is:

1. A panoramic x-ray system comprising:
  a gantry;
  at least one x-ray source mounted on the gantry and configured to selectively output x-ray radiation having a first energy characteristic and x-ray radiation having a second energy characteristic, the second energy characteristic being different from the first energy characteristic;
  a controller configured to control the at least one x-ray source to produce x-ray radiation having the first energy characteristic during a first time period and to produce x-ray radiation having the second energy characteristic during a second time period temporally adjacent to the first time period; and
  a receptor configured to generate an image data set comprising a plurality of image frames including a first frame and a second frame, the receptor mounted on the gantry and positioned to receive x-ray radiation from the at least one x-ray source, wherein the receptor is configured to output the first frame of the image data set based on x-ray radiation received during the first time period at a first gantry position and the second frame of the image data set based on x-ray radiation received during the second time period at a second gantry position successive to the first position,
  wherein the x-ray source selectively switches outputting x-ray radiation having the first energy characteristic and the second energy characteristic at a rate of at least 100 times per second and
  wherein the gantry is controlled to move the x-ray source and the receptor along a path so that the image data set includes a panoramic image data set that has a curved plane centered on a patient's anatomy.

2. A panoramic x-ray system as claimed in claim 1, wherein the at least one x-ray source comprises a cathode and an anode configured to be selectively coupled to a first voltage source and a second voltage source, the at least one x-ray source configured to output x-ray radiation having the first energy characteristic when the anode is coupled to the first voltage source, the at least one x-ray source further configured to output x-ray radiation having the second energy characteristic when the anode is coupled to the second voltage source.

3. A panoramic x-ray system as claimed in claim 1, wherein the at least one x-ray source comprises:
  a cathode;
  an anode configured to be selectively coupled to a first voltage source and a second voltage source, the at least one x-ray source configured to output x-ray radiation having the first energy characteristic when the anode is coupled to the first voltage source, the at least one x-ray source further configured to output x-ray radiation having the second energy characteristic when the anode is coupled to the second voltage source; and a switching arrangement including at least one high voltage switch, the switching arrangement configured to alternatingly couple the anode to the first and second voltage sources.

4. A panoramic x-ray system as claimed in claim 1, wherein the x-ray source comprises:
   a cathode;
   an anode;
   at least one voltage source configured to alternatingly output a first voltage during the first time period and a second voltage during the second time period, the second voltage being different from the first voltage, wherein the at least one x-ray source is configured to produce the x-ray radiation having the first energy characteristic when the first voltage is applied between the cathode and the anode, and wherein the at least one x-ray source is configured to produce the x-ray radiation having the second energy characteristic when the second voltage is applied between the cathode and the anode.

5. A panoramic x-ray system as claimed in claim 1, wherein the at least one x-ray source comprises an x-ray tube and a movable filter having at least first and second filter portions, the x-ray tube configured to produce x-ray radiation, and wherein the filter is configured to alternatingly move the first and second filter portions into position to filter the x-ray radiation produced by the x-ray tube.

6. A panoramic x-ray system as claimed in claim 1, wherein the at least one x-ray source comprises a first x-ray source and a second x-ray source, wherein the first x-ray source is configured to generate x-ray radiation having the first energy characteristic, and wherein the second x-ray source is configured to generate x-ray radiation having the second energy characteristic.

7. A panoramic x-ray system as claimed in claim 1, wherein the at least one x-ray source comprises a movable anode having first and second positions, wherein the at least one x-ray source is configured to produce x-ray radiation having the first energy characteristic when the anode is in the first position, and wherein the at least one x-ray source is configured to produce x-ray radiation having the second energy characteristic when the anode is in the second position.

8. A panoramic x-ray system as claimed in claim 1, wherein the at least one x-ray source comprises a first cathode coupled to a first voltage source and a second cathode coupled to a second voltage source, wherein the at least one x-ray source is configured to output x-ray radiation having the first energy characteristic when electrons are emitted from the first cathode, and wherein the at least one x-ray source is configured to output x-ray radiation at the second energy level when electrons are emitted from the second cathode.

9. A panoramic x-ray system as claimed in claim 1, wherein the at least one x-ray source comprises a plurality of anodes, each of the plurality of anodes having a different voltage.

10. A panoramic x-ray system as claimed in claim 1, wherein the at least one x-ray source comprises:
    a cathode;
    first and second anodes, each having a different voltage; and
    at least one electron deflecting electrode configured to selectively guide electrons to one of the first and second anodes, wherein the at least one x-ray source is configured to generate x-ray radiation having the first energy characteristic when the electrons are guided to the first anode, and wherein the at least one x-ray source is configured to generate x-ray radiation having the second energy characteristic when the electrons are guided to the second anode.

11. A panoramic x-ray system as claimed in claim 1, wherein the at least one x-ray source comprises:
    a cathode;
    first and second anodes, each having a different voltage; and
    at least one electron deflecting magnet configured to selectively guide electrons to one of the first and second anodes, wherein the at least one x-ray source is configured to generate x-ray radiation having the first energy characteristic when the electrons are guided to the first anode, and wherein the at least one x-ray source is configured to generate x-ray radiation having the second energy characteristic when the electrons are guided to the second anode.

12. A panoramic x-ray system as claimed in claim 1, wherein the at least one x-ray source comprises:
    a cathode; and
    a light source configured to illuminate the cathode.

13. A panoramic x-ray system as claimed in claim 1, wherein the at least one x-ray source comprises a cathode comprising a nanostructured material.

14. A panoramic x-ray system as claimed in claim 1, wherein the at least one x-ray source comprises a plurality of anodes, each of the plurality of anodes comprising a different material.

15. A panoramic x-ray system comprising:
    a gantry;
    an x-ray source mounted on the gantry and configured to output x-ray radiation having a plurality of energies, the plurality of energies including first and second energies; and
    a detector panel mounted on the gantry and positioned to receive x-ray radiation from the x-ray source, the detector panel configured to distinguish between radiation having the first energy and radiation having the second energy and to output a plurality of image frames of data including a first frame based on detection of the radiation at a first gantry position having the first energy, and the second frame based on detection of the radiation at a second gantry position successive to the first position having the second energy, the second frame being temporally adjacent to the first frame,
    wherein the x-ray source selectively switches outputting x-ray radiation having the first energy characteristic and the second energy characteristic at a rate of at least 100 times per second and
    wherein the gantry is controlled to move the x-ray source and the receptor along a path so that the image data set includes a panoramic image data set that has a curved plane centered on a patient's anatomy.

16. A method of obtaining a panoramic image, the method comprising:
    generating x-ray radiation having a first energy characteristic;
    detecting, with a receptor mounted on a gantry, a first frame of image data based on the x-ray radiation having the first energy characteristic;
    generating x-ray radiation having a second energy characteristic;
    detecting, with the receptor, a second frame of image data, the second frame being temporally adjacent to the first frame and based on the x-ray radiation having the second energy characteristic impinging the receptor;

rotating the gantry; and
generating a panoramic image based at least in part on the first and second frames of image data,
wherein the x-ray radiation is selectively switched between the first energy characteristic and the second energy characteristic at a rate of at least 100 times per second and wherein the gantry is controlled to move the x-ray source and the receptor along a path so that the image data set includes a panoramic image data set that has a curved plane centered on a patient's anatomy.

17. The method of obtaining a panoramic image as claimed in claim 16, wherein the step of generating x-ray radiation having a first energy characteristic comprises:
    (a) applying a first voltage between a cathode and an anode; and
    (b) using the first voltage to accelerate a first stream of electrons from the cathode to the anode to generate the x-ray radiation having the first energy characteristic, and wherein the step of generating x-ray radiation having a second energy characteristic comprises:
    (c) applying a second voltage between the cathode and the anode, the second voltage being different from the first voltage; and
    (d) using the second voltage to accelerate a second stream of electrons from the cathode to the anode to generate the x-ray radiation having the second energy characteristic.

18. The method of obtaining a panoramic image as claimed in claim 17, further comprising repeating steps (a) through (d) until a full scan is complete.

19. The method of obtaining a panoramic image as claimed in claim 16, wherein the step of generating x-ray radiation having a first energy characteristic comprises applying a first voltage to at least one x-ray source to produce x-ray radiation, and wherein the step of generating x-ray radiation having a second energy characteristic comprises applying a second voltage to the at least one x-ray source to produce x-ray radiation, the second voltage being different from the first voltage.

20. The method of obtaining a panoramic image as claimed in claim 16, wherein the step of generating x-ray radiation having a first energy characteristic comprising:
    activating an x-ray source to produce x-ray radiation; and
    positioning a moving filter to receive the x-ray radiation through a first section of the moving filter to produce x-ray radiation having the first energy characteristic, and wherein the step of generating x-ray radiation having a second energy characteristic comprises:
    positioning the moving filter to receive the x-ray radiation through a second section of the moving filter to generate x-ray radiation having the second energy characteristic.

21. The method of obtaining a panoramic image as claimed in claim 16, wherein the step of generating x-ray radiation having a first energy characteristic comprises:
    activating a first x-ray source configured to produce the x-ray radiation having the first energy characteristic; and
    deactivating the first x-ray source after the x-ray radiation having the first energy characteristic has been detected, and wherein the step of generating x-ray radiation having a second energy characteristic comprises:
    activating a second x-ray source configured to produce the x-ray radiation having the second energy characteristic; and
    deactivating the second x-ray source after the x-ray radiation having the second energy characteristic has been detected.

22. The method of obtaining a panoramic image as claimed in claim 16, wherein the step of generating x-ray radiation having a first energy characteristic comprises:
    emitting a first electron stream from a cathode;
    positioning a moving anode to receive the first electron stream at a first section of the anode to produce the x-ray radiation having the first energy characteristic, and wherein the step of generating x-ray radiation having a second energy characteristic comprises:
    emitting a second electron stream from the cathode; and
    positioning the moving anode to receive the electron stream at a second section of the anode to produce the x-ray radiation having the second energy characteristic.

23. The method of obtaining a panoramic image as claimed in claim 16, wherein the step of generating x-ray radiation having a first energy characteristic comprises:
    applying a first voltage between a first cathode and at least one anode; and
    accelerating, by the first voltage, a first electron stream from the first cathode to the at least one anode to generate the x-ray radiation having the first energy characteristic, and wherein the step of generating x-ray radiation having a second energy characteristic comprises
    applying a second voltage between a second cathode and the at least one anode; and
    accelerating, by the second voltage, a second electron stream from the second cathode to the at least one anode to produce the x-ray radiation having the second energy characteristic.

24. The method of obtaining a panoramic image as claimed in claim 16, wherein the step of generating x-ray radiation having a first energy characteristic comprises:
    applying a first voltage to a first cathode;
    applying a second voltage to a first anode; and
    generating an electron stream interacting with the first anode to generate x-ray radiation having the first energy characteristic, and wherein the step of generating x-ray radiation having a second energy characteristic comprises:
    applying a third voltage to a second anode;
    applying at least one of the first voltage and a fourth voltage to a second cathode; and
    generating an electron stream interacting with the second anode to generate x-ray radiation having a second energy characteristic.

25. The method of obtaining a panoramic image as claimed in claim 16, wherein the step of generating x-ray radiation having a first energy characteristic comprises:
    applying a first voltage to a cathode;
    applying a second voltage to a first anode;
    generating an electron stream from the cathode; and
    activating at least one electron deflecting electrode to guide the electron stream to the first anode to generate x-ray radiation having the first energy characteristic, and wherein the step of generating x-ray radiation having a second energy characteristic comprises:
    applying a third voltage to a second anode;
    activating the at least one electron deflecting electrode to guide the electron stream to the second anode to generate x-ray radiation having the second energy characteristic.

26. The method of obtaining a panoramic image as claimed in claim 16, wherein the step of generating x-ray radiation having a first energy characteristic comprises:
applying a first voltage to a cathode;
applying a second voltage to a first anode;
generating an electron stream from the cathode; and
activating at least one electron deflecting magnet to guide the electron stream to the first anode to generate x-ray radiation having the first energy characteristic, and wherein the step of generating x-ray radiation having a second energy characteristic comprises:
applying a third voltage to a second anode;
activating the at least one electron deflecting magnet to guide the electron stream to the second anode to generate x-ray radiation having the second energy characteristic.

27. The method of obtaining a panoramic image as claimed in claim 16, wherein generating a panoramic image includes combining at least a portion of the first frame and at least a portion of the second frame using a subtraction operation.

28. The method of obtaining a panoramic image as claimed in claim 16, further comprising providing at least one x-ray source comprising at least one light-activatable cathode and at least one anode, wherein each of the generating steps comprises illuminating the at least one cathode with light.

29. The method of obtaining a panoramic image as claimed in claim 16, further comprising providing an x-ray source comprising a cathode and an anode, the cathode comprising a nanostructured material.

30. The method of obtaining a panoramic image as claimed in claim 16, wherein each of the generating steps comprises turning on x-ray emission from at least one x-ray source, the method further comprising:
after the step of detecting the first frame and before the step of generating the x-ray radiation having the second energy characteristic, turning off the emission from the at least one x-ray source.

31. A method of obtaining a panoramic image, the method comprising:
generating x-ray radiation having a plurality of energies, the plurality of energies including first and second energies;
directing the x-ray radiation toward a subject;
a first step of detecting, with a detector panel mounted on a gantry, a first portion of x-ray radiation passing through the subject, the first portion including a first component of x-ray radiation having the first energy and a second component of x-ray radiation having the second energy, the detector panel configured to distinguish between radiation having the first energy and radiation having the second energy, the first detecting step comprising:
a first step of distinguishing between the first and second x-ray components, and outputting first and second image frames of data, the first image frame based on at least the first component, and the second image frame, being temporally adjacent to the first image data, based at least on the second component;
changing an angular position of the gantry after the first detecting step; and
a second step of detecting, with the detector panel, a second portion of x-ray radiation passing through the subject, the second portion including a third component of x-ray radiation having the first energy and a fourth component of x-ray radiation having the second energy, the second detecting step occurring after the step of changing the angular position, the second detecting step comprising
a second step of distinguishing between the third and fourth components, and
outputting third and fourth image frames of data, the third image frame based on at least the third component, and the fourth image frame based at least on the fourth component
wherein the x-ray radiation is selectively switched between the first energy characteristic and the second energy characteristic at a rate of at least 100 times per second and
wherein the gantry is controlled to move the x-ray source and the receptor along a path so that the image data set includes a panoramic image data set that has a curved plane centered on a patient's anatomy.

32. The method of obtaining a panoramic image as claimed in claim 31, further comprising:
combining at least a portion of the first image frame and at least a portion of the second image frame using a subtraction operation; and
combining at least a portion of the third image frame and at least a portion of the fourth image frame using a subtraction operation.

33. A panoramic x-ray system comprising:
a gantry;
at least one x-ray source mounted on the gantry and configured to output x-ray radiation;
a controller configured to control the at least one x-ray source to produce x-ray radiation; and
a detector mounted on the gantry and positioned to receive x-ray radiation from the at least one x-ray source, the detector including a first receptor and a second receptor, the first receptor configured to output a first frame of image data based on x-ray radiation of a first energy spectrum and the second receptor configured to output a second frame of image data based on x-ray radiation of a second energy spectrum, the second frame being temporally adjacent to the first frame
wherein the x-ray source selectively switches outputting x-ray radiation having the first energy characteristic and the second energy characteristic at a rate of at least 100 times per second and
wherein the gantry is controlled to move the x-ray source and the receptor along a path so that the image data set includes a panoramic image data set that has a curved plane centered on a patient's anatomy.

34. The system as claimed in claim 33, the detector further comprising a filter positioned between the first receptor and the second receptor.

35. A method of obtaining a panoramic image, the method comprising:
generating x-ray radiation;
detecting, with a detector mounted on a gantry and having a first receptor and a second receptor, a first frame of image data with the first receptor based on the x-ray radiation having a first energy characteristic;
detecting, with the second receptor, a second frame of image data based on the x-ray radiation having a second energy characteristic different than the first energy characteristic, the second image frame being temporally adjacent to the first image data;
rotating the gantry; and
generating a panoramic image based at least in part on the first and second frames of image data wherein the x-ray radiation is selectively switched between the first energy characteristic and the second energy characteristic at a rate of at least 100 times per second and wherein the gantry is controlled to move the x-ray source and the receptor along a path so that the image data set includes a panoramic image data set that has a curved plane centered on a patient's anatomy.

36. The method as claimed in claim 35, the method further comprising filtering radiation between the first receptor and the second receptor.

37. A panoramic x-ray system as claimed in claim 1, wherein the x-ray source selectively switches outputting radiation having the first energy characteristic and the second energy characteristic at a rate of 100 to 400 times per second.

38. A panoramic x-ray system as claimed in claim 15, wherein the x-ray source selectively switches outputting x-ray radiation having the first energy characteristic and the second energy characteristic at a rate of 100 to 400 times per second.

39. The method of obtaining a panoramic image as claimed in claim 16, wherein the x-ray radiation is selectively switched at a rate of 100 to 400 times per second.

40. The method of obtaining a panoramic image as claimed in claim 31, wherein the x-ray radiation is selectively switched at a rate of 100 to 400 times per second.

41. The system as claimed in claim 33, wherein the x-ray source selectively switches outputting x-ray radiation having the first energy characteristic and the second energy characteristic at a rate of approximately 100 to 400 times per second.

42. The method as claimed in claim 35, wherein the x-ray radiation is selectively switched at a rate of 100 to 400 times per second.

* * * * *